(12) United States Patent
Ring et al.

(10) Patent No.: US 11,890,450 B2
(45) Date of Patent: Feb. 6, 2024

(54) BACKFLOW PREVENTION MECHANISM FOR DRUG DELIVERY DEVICE

(71) Applicant: AMGEN INC., Thousand Oaks, CA (US)

(72) Inventors: Lawrence Scott Ring, Laguna Beach, CA (US); Tohid Pirbodaghi, Cambridge, MA (US); Samin Akbari, Cambridge, MA (US); Daniel Eduardo Groszmann, Belmont, MA (US); Mehran Mojarrad, Thousand Oaks, CA (US); Mark Gordon, Thousand Oaks, CA (US); Mikhail Tikh, St. Louis Park, MN (US); Jimmie L. Ward, Golden, CO (US); Scott R. Gibson, Granada Hills, CA (US); Sheldon B. Moberg, Thousand Oaks, CA (US); Joshua Tamsky, Los Angeles, CA (US); Paul Faucher, Escondido, CA (US); Jeff Lind, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 396 days.

(21) Appl. No.: 16/297,408

(22) Filed: Mar. 8, 2019

(65) Prior Publication Data

US 2019/0275241 A1    Sep. 12, 2019

Related U.S. Application Data

(60) Provisional application No. 62/640,934, filed on Mar. 9, 2018.

(51) Int. Cl.
*A61M 5/168* (2006.01)
*A61M 5/14* (2006.01)
(Continued)

(52) U.S. Cl.
CPC ...... *A61M 5/16813* (2013.01); *A61M 5/1413* (2013.01); *A61M 5/14248* (2013.01);
(Continued)

(58) Field of Classification Search
CPC ............ A61M 5/16813; A61M 5/1413; A61M 5/14248; A61M 5/158; A61M 39/24;
(Continued)

(56) References Cited

U.S. PATENT DOCUMENTS

| 5,308,333 | A | 5/1994 | Skakoon |
| 5,957,895 | A | 9/1999 | Sage et al. |

(Continued)

FOREIGN PATENT DOCUMENTS

| JP | 2006021055 A | 1/2006 |
| JP | 2016504150 A | 2/2016 |

(Continued)

OTHER PUBLICATIONS

International Application No. PCT/US19/021472, International Search Report and Written Opinion, dated May 21, 2019.
(Continued)

*Primary Examiner* — Tasnim Mehjabin Ahmed
(74) *Attorney, Agent, or Firm* — MARSHALL, GERSTEIN & BORUN LLP; Michael P. Furmanek

(57) ABSTRACT

A drug delivery device includes a housing defining a shell and an inner volume, a container, a drive mechanism, a needle assembly, a fluid flow connection, and a backflow prevention mechanism. The container has an inner volume to contain a medicament to be administered to a user. The drive mechanism is at least partially disposed within the housing and exerts a force to urge the medicament out the container. The fluid flow connection is coupled to the container and the needle assembly and allows the medicament to flow from the container to the needle assembly to be
(Continued)

administered. The backflow prevention mechanism is associated with at least one of the container, the fluid flow connection, or the needle assembly and includes at least one flow restrictor to restrict a fluid from flowing from the needle assembly to the container.

16 Claims, 15 Drawing Sheets

(51) Int. Cl.
*A61M 5/142* (2006.01)
*A61M 5/158* (2006.01)
*A61M 39/24* (2006.01)
*A61M 5/145* (2006.01)
*A61M 5/155* (2006.01)

(52) U.S. Cl.
CPC ........ *A61M 5/158* (2013.01); *A61M 5/16822* (2013.01); *A61M 39/24* (2013.01); *A61M 5/14526* (2013.01); *A61M 5/155* (2013.01); *A61M 2005/1403* (2013.01); *A61M 2005/1406* (2013.01); *A61M 2005/14252* (2013.01); *A61M 2039/244* (2013.01); *A61M 2039/2406* (2013.01); *A61M 2039/248* (2013.01); *A61M 2039/2426* (2013.01); *A61M 2205/3561* (2013.01); *A61M 2205/505* (2013.01); *A61M 2205/7527* (2013.01); *A61M 2205/7536* (2013.01); *A61M 2209/045* (2013.01)

(58) Field of Classification Search
CPC ........... A61M 2005/14252; A61M 2005/1406; A61M 2039/248; A61M 2039/2406; A61M 2039/2426
See application file for complete search history.

(56) References Cited

U.S. PATENT DOCUMENTS

| | | | | |
|---|---|---|---|---|
| 6,120,492 | A * | 9/2000 | Finch | A61M 39/0208 604/502 |
| 2002/0123740 | A1* | 9/2002 | Flaherty | A61M 5/1452 604/93.01 |
| 2003/0229310 | A1* | 12/2003 | Flaherty | A61M 5/1452 604/151 |
| 2004/0010207 | A1* | 1/2004 | Flaherty | A61B 5/157 600/573 |
| 2007/0233019 | A1* | 10/2007 | Forsell | A61M 5/14276 604/288.03 |
| 2012/0078197 | A1 | 3/2012 | O'Connor et al. | |
| 2012/0330235 | A1* | 12/2012 | Moga | A61M 5/14248 604/131 |
| 2015/0328401 | A1 | 11/2015 | Lynch et al. | |

FOREIGN PATENT DOCUMENTS

| | | |
|---|---|---|
| WO | WO-02/40083 A2 | 5/2002 |
| WO | WO-2014116274 A1 | 7/2014 |
| WO | WO-2017/139741 A1 | 8/2017 |

OTHER PUBLICATIONS

"Intravenous Infusion Lines, Enhancing Patient Safety During IV Therapy", Vygon (UK) Ltd, 1-7 (2010).
"Saflo Microvolume Extension Set", Applied Medical Technology Ltd, (2020).
Lintel et al., "High-Throughput Micro-Debubblers for Bubble Removal with Sub-Microliter Dead Volume", Micromachines, 3: 218-224 (2012).
Japanese Patent Application No. 2020-542136, Office Action, dated Jan. 17, 2023.
Japanese Patent Application No. 2020-542136, Examiner's Decision of Rejection, dated Aug. 15, 2023.

* cited by examiner

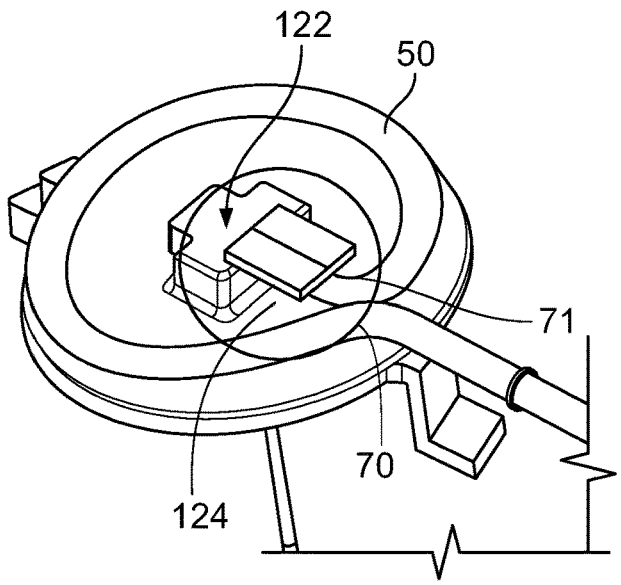
FIG. 3A
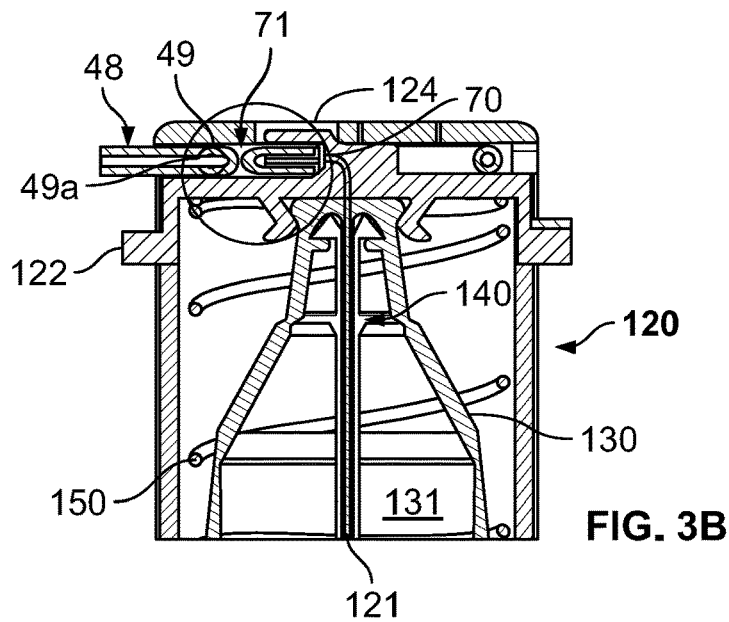
FIG. 3B
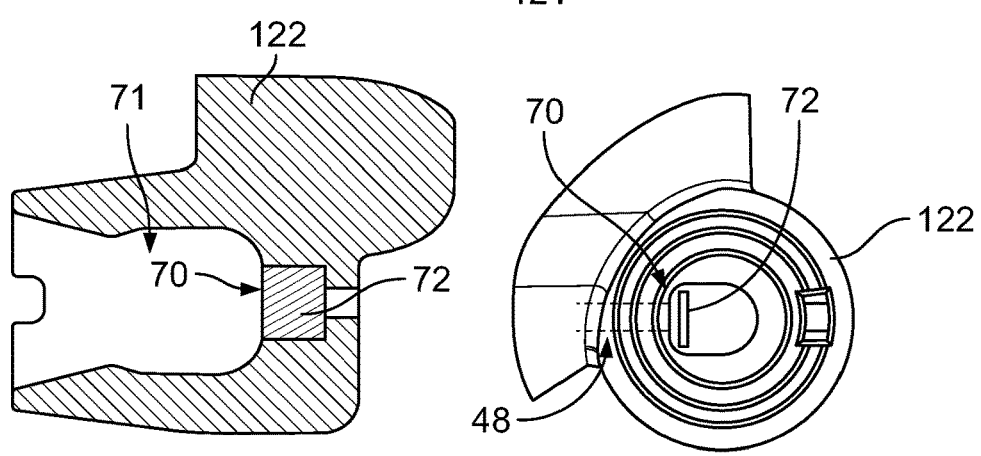
FIG. 4A  FIG. 4B

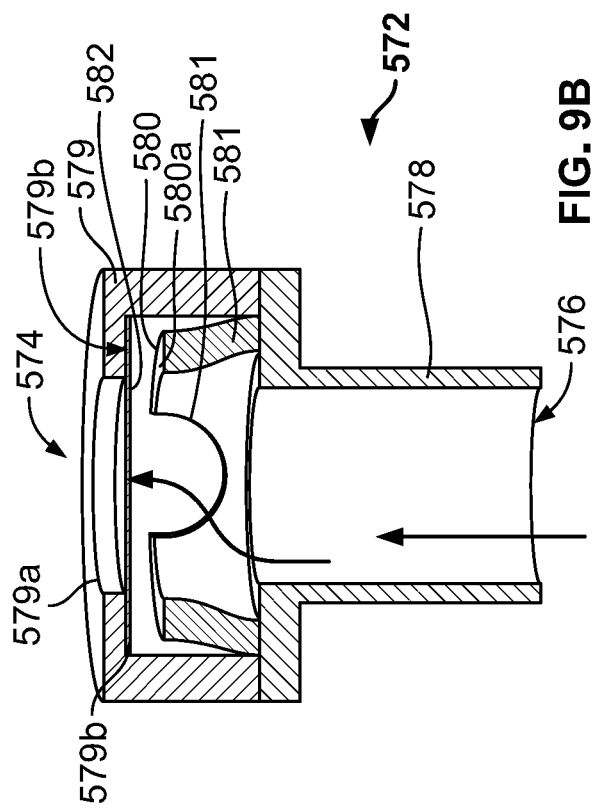
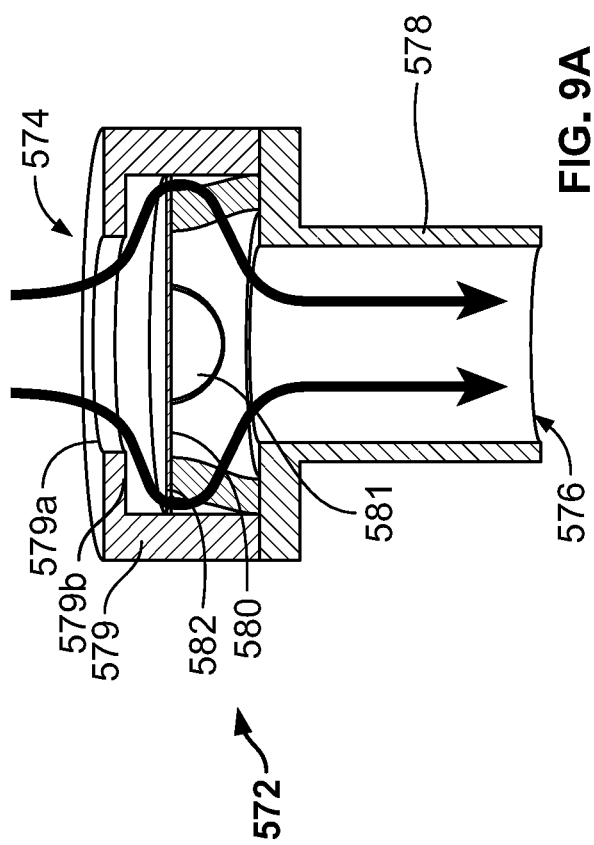
FIG. 9B
FIG. 9A

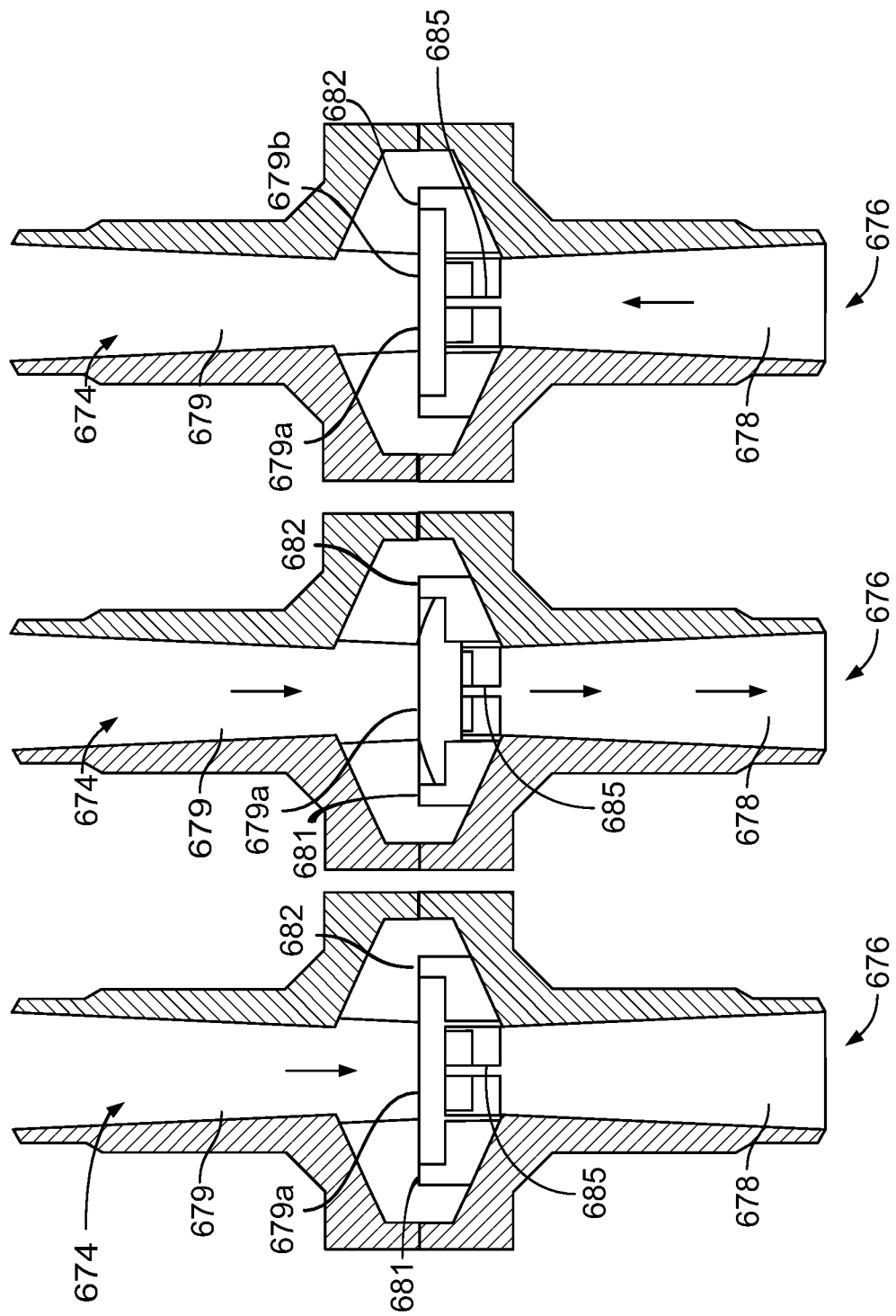

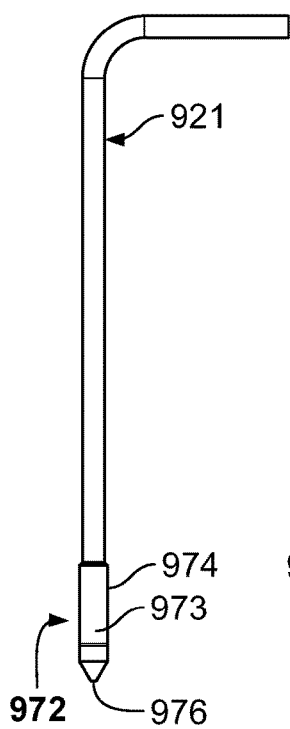 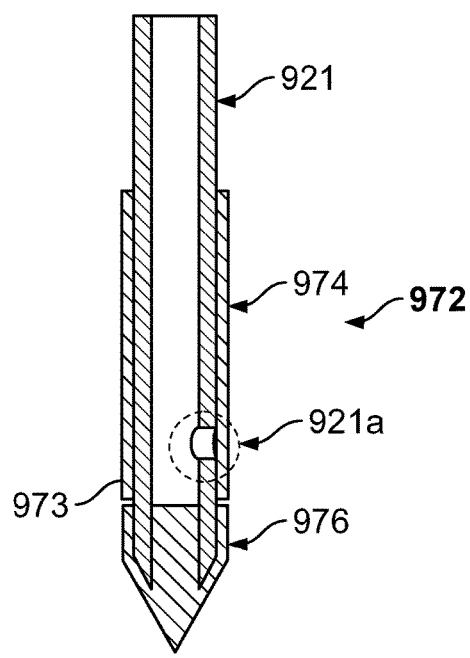 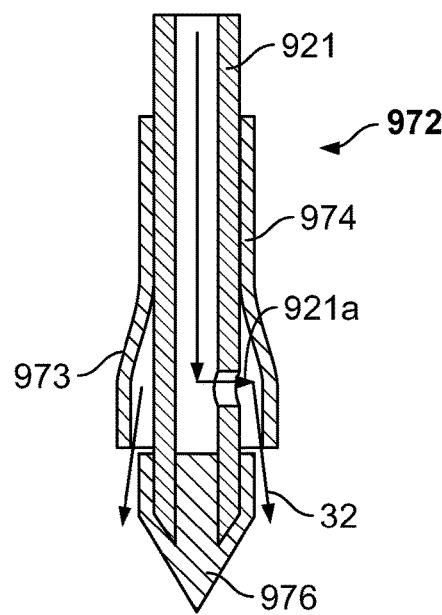
FIG. 14A  FIG. 14B  FIG. 14C
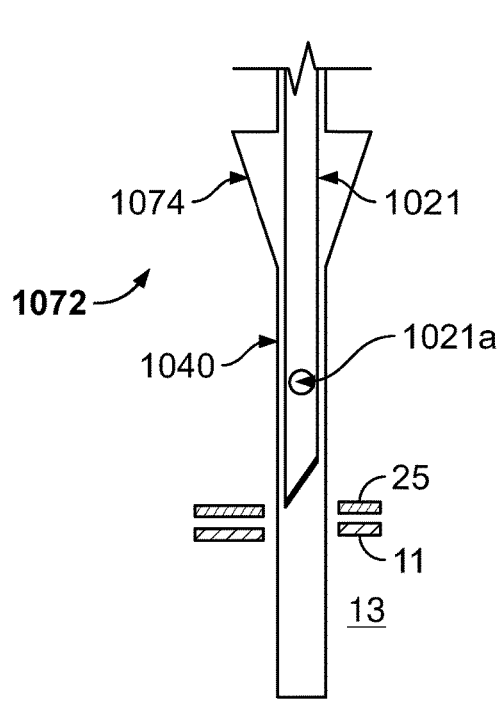 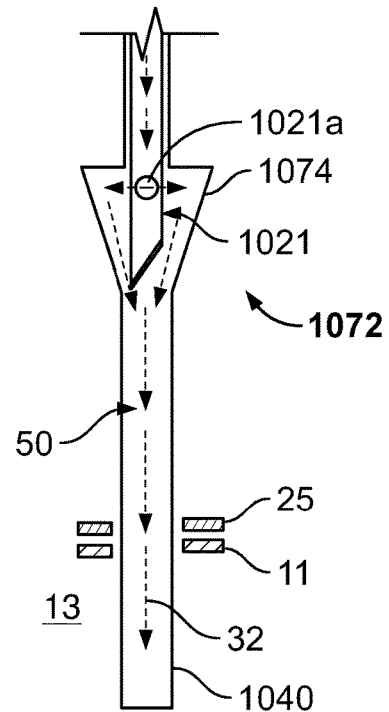
FIG. 15A  FIG. 15B

BACKFLOW PREVENTION MECHANISM FOR DRUG DELIVERY DEVICE

CROSS-REFERENCE TO RELATED APPLICATIONS

This application claims the benefit of U.S. Provisional Application No. 62/640,934, filed on Mar. 9, 2018, the entirety of which is herein expressly incorporated by reference.

FIELD OF DISCLOSURE

The disclosure relates to drug delivery devices and, more particularly, to drug delivery devices having backflow prevention mechanisms to assist in drug flow.

BACKGROUND

Drug delivery devices, such as injectors, are used to deliver liquid drugs to a patient. Upon activation, a drug delivery device will expel a drug stored within an internal reservoir through a needle, cannula, or other delivery member into the patient. Some drug delivery devices, such as on-body injectors, may be temporarily attached to a patient to deliver a drug via an injection needle or some other means over an extended period of time. The drug delivery device may be adhesively attached to the tissue of the patient's abdomen, thigh, arm, or some other portion of the patient's body.

Delayed delivery devices may enhance therapeutic efficacy of certain drugs while preventing adverse side effects. Such devices may first be activated by a healthcare professional, thereby causing a needle and/or a cannula to be inserted into a patient's tissue, but may not actually administer the drug for an extended period. In some cases, backflow of bodily fluids into drug delivery devices can result in occlusions of the fluid path. Clots may form along the fluid path of the drug delivery device as a result of the backflow of blood or other fluids. The coagulated material may prevent the drug from being delivered when the pressure required to push the medication through the clot (or to alternatively displace the clot) exceeds the drive force capability of the device. Accordingly, the device may stall, which can adversely impact delivery of the drug to the user.

SUMMARY

One aspect of the present disclosure provides a drug delivery device that includes a housing defining a shell and an inner volume, a container, a drive mechanism, a needle assembly, a fluid flow connection, and a backflow prevention mechanism. The container has an inner volume to contain a medicament to be administered to a user. The drive mechanism is at least partially disposed within the housing and exerts a force to urge the medicament out of the container. The fluid flow connection is coupled to the container and the needle assembly and allows the medicament to flow from the container to the needle assembly to be administered. The backflow prevention mechanism is associated with at least one of the container, the fluid flow connection, or the needle assembly and includes at least one flow restrictor to restrict a fluid from flowing from the needle assembly toward the container.

In some examples, the at least one flow restrictor may include a one-way valve. In some examples, the flow restrictor may be any one of a slit valve, an umbrella valve, a ball valve, a duckbill valve, or a flap valve. In some examples, any number of these valves may be used in combination with each other.

In some forms, the backflow prevention mechanism may be disposed at a coupling region at which the fluid flow connection is coupled to the needle assembly. The coupling region may include a ball and reservoir receptacle adapted to seal the needle assembly. In other forms, the backflow prevention mechanism is at least partially disposed within the needle assembly.

In some embodiments, the fluid flow connection may be constructed from a flexible tube (e.g., a polymer material). Other suitable materials may additionally be used.

A second aspect of the present disclosure provides a backflow prevention mechanism for a drug delivery device. The backflow prevention mechanism is associated with at least one of a container, a fluid flow connection, or a needle assembly of the drug delivery device. In this aspect, the backflow prevention mechanism may include at least one flow restrictor that restricts a fluid from flowing from the needle assembly to the container.

A third aspect of the present disclosure provides a method of preventing backflow in a drug delivery device having a housing defining a shell and an inner volume and a container at least partially disposed within the inner volume of the housing and being adapted to contain a medicament to be administered to a user. A drive mechanism is at least partially disposed within the housing to exert a force to urge the medicament out of the container. A needle assembly is also at least partially disposed within the housing. A fluid flow connection is coupled to the container and the needle assembly to allow the medicament to flow from the container to the needle assembly. A backflow prevention mechanism is associated with at least one of the container, the fluid flow connection, or the needle assembly. The backflow prevention mechanism includes at least one flow restrictor to restrict a fluid from flowing from the needle assembly to the container.

BRIEF DESCRIPTION OF THE DRAWINGS

The above needs are at least partially met through provision of the backflow prevention mechanism for a drug delivery device described in the following detailed description, particularly when studied in conjunction with the drawings, wherein:

The accompanying figures show embodiments according to the disclosure and are exemplary rather than limiting.

FIG. 3A illustrates a perspective view of a fluid flow path coupled to a needle hub assembly of a drug delivery device in accordance with various embodiments;

FIG. 3B illustrates a side cross-sectional view of the fluid flow path being coupled to the needle hub assembly as illustrated in FIG. 3A in accordance with various embodiments;

FIGS. 4A and 4B illustrate side and top cross-sectional views, respectively, of an example placement of the backflow prevention mechanism of a drug delivery device in accordance with various embodiments;

FIGS. 9A and 9B illustrate side cross-sectional views of a fifth example backflow prevention mechanism in the form of a flap valve in accordance with various embodiments;

FIGS. 10A-10C illustrate side cross-sectional views of a sixth alternative backflow prevention mechanism in the form of a flap valve in accordance with various embodiments;

FIGS. 14A-14C illustrate side elevation and cross-sectional views of a ninth alternate backflow prevention mechanism using a sleeve valve assembly in accordance with various embodiments;

FIGS. 15A-15H illustrate side elevation and cross-sectional views of a tenth alternate backflow prevention mechanism using a sleeve valve assembly in accordance with various embodiments.

Figures 1, 2:
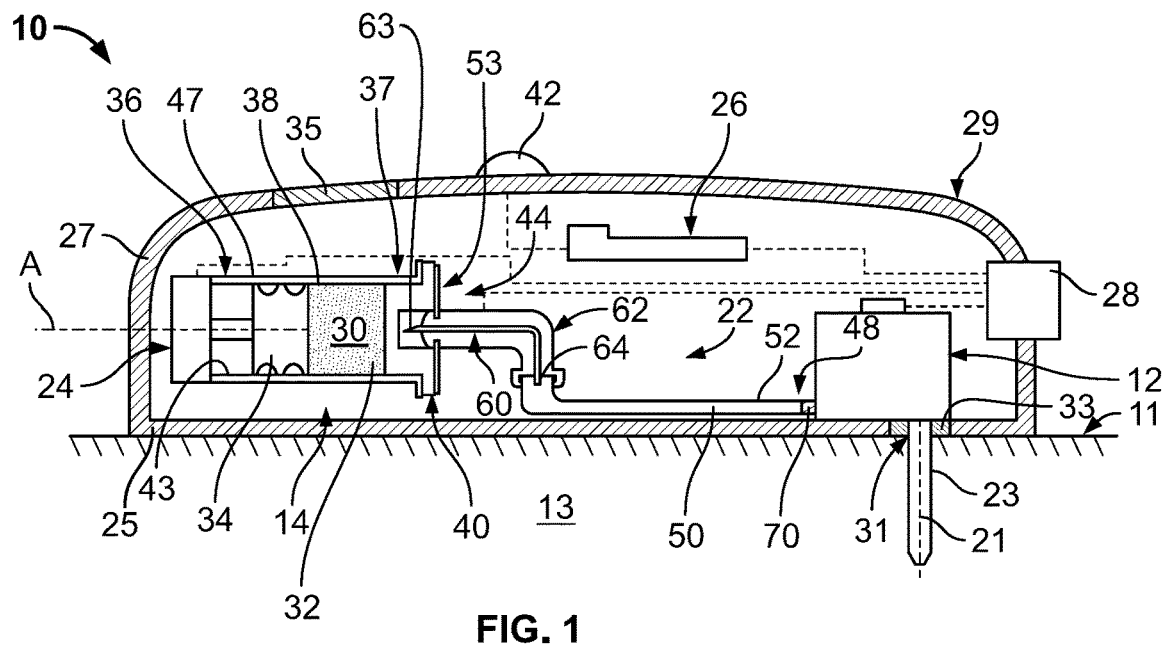
FIG. 1 illustrates a schematic cross-sectional view of an embodiment of a drug delivery device in accordance with various embodiments.
FIG. 2 illustrates a perspective view of the drug delivery device of FIG. 1 showing a fluid flow path connection to a needle assembly in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a backflow prevention mechanism for a drug delivery device. Generally, the drug delivery device includes a housing defining a shell, a container, a drive mechanism, a needle assembly having first and second ends, a fluid flow connection, and a backflow prevention mechanism, each of which is at least partially disposed within the housing. The container has first and second ends and an inner volume to contain a medicament to be administered to a user. The drive mechanism is adapted to exert a force on the first end of the container to urge the medicament through the container towards the second end thereof. The fluid flow connection is coupled to the second end of the container and the first end of the needle assembly and is adapted to allow the medicament to flow from the container to the needle assembly.

The backflow prevention mechanism is a fluid path element disposed in the fluid path. The backflow prevention mechanism permits fluid flow in a first direction (i.e., from the container to the needle assembly to allow the drug to be administered to the patient) while restricting fluid flow in a second direction (i.e., from the needle assembly back toward the container). By preventing fluid flow in the second direction, the likelihood of clot formation is reduced and/or eliminated; thereby ensuring fluid may flow at flow rates. As a result, the backflow prevention mechanism may eliminate the need for costly, high powered drive mechanisms needed to overcome flow path blockages, as well as blockages that prevent drug delivery entirely. Further, the backflow prevention mechanisms may be readily employed in delayed delivery injectors that do not immediately deliver the drug to the patient at the time that the device is activated and/or the needle and/or cannula is inserted into the patient.

FIG. 1 is a schematic illustration of one embodiment of a drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, and is releasably attachable to the patient's tissue 11 (e.g., the patient's skin). The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include a needle assembly (also referred to as an insertion mechanism) 12, a container 14, a fluid pathway assembly 22, a drive mechanism 24, and a controller 26, each of which may be disposed within an interior space of a main housing 29 that defines a shell. An actuator 28 (e.g., a user-depressible button, touchscreen, microphone, etc.) may protrude through or otherwise be disposed at an exterior surface of the housing 29 and may be configured to initiate operation of the drug delivery device 10 by activating, via mechanical and/or electrical means (shown in dotted lines in FIG. 1), the needle assembly 12, the fluid pathway assembly 22, the drive mechanism 24, the controller 26, and/or other mechanisms and/or electronics. In some examples, wireless communication may be employed to cause the device 10 to be activated. In embodiments where the actuator 28 is a button that is depressed or otherwise physically moved by a user or patient, the actuator 28 may be configured to exert a motive force needed to activate the needle assembly 12, the fluid pathway assembly 22, the drive assembly 24, the controller 26, and/or other mechanisms. In such embodiments, the actuator 28 may be physically connected to, either directly or indirectly via a mechanical linkage, the needle assembly 12, the drive mechanism 24, the fluid pathway assembly 22, and/or other mechanisms such that manually depressing or otherwise interacting with the actuator 28 supplies the motive force necessary to activate the needle assembly 12, the drive mechanism 24, the fluid pathway assembly 22, and/or other mechanisms. For example, in some embodiments, manually depressing the actuator 28 may cause the fluid pathway assembly 22 to move towards a first end 36 of the stationary container 14, or cause the container 14 to move towards the stationary fluid pathway assembly 22, and thereby cause a container access needle 60 to penetrate through a seal member 40 into a reservoir or interior volume 30 of the container 14. Additionally, or alternatively, the actuator 28 may operate as an input device that transmits an electrical and/or mechanical signal to the controller 26, which in turn may execute programmable instructions to control operation of the needle assembly 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the needle assembly 12, the drive mechanism 24, the fluid pathway assembly 22, and/or other mechanisms.

Still referring to FIG. 1, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 14 and a drug 32 contained therein. The one or more visual indicators 42 may be used to communicate information to the user about the operational state of the drug delivery device 10 and/or the condition of the medicament or drug 32. An opening 31 may be formed in the bottom wall 25, and optionally a pierceable sterile barrier 33, such as a pierceable septum, may extend across the opening 31 to seal the interior of the housing 29 prior to use. In some embodiments, the pierceable sterile barrier 33 may be omitted, and instead a removable sealing member (not illustrated) may cover and seal closed the opening 31 prior to use.

After the bottom wall 25 of the housing 29 is attached to the patient's skin 11, the needle assembly 12 may be activated to move a delivery member from a retracted position within the housing 29 to a deployed position extending outside of the housing 29. In the present embodiment, this may include the needle assembly 12 inserting a needle or trocar 21 and a hollow cannula 23 surrounding the trocar 21 through the pierceable sterile barrier 33 and into the patient's skin 11 and subcutaneous tissue 13, as illustrated in FIG. 1. Immediately or shortly thereafter, the needle assembly 12 may automatically retract the needle 21, leaving the distal open end of the cannula 23 inside the patient for subcutaneous delivery of the drug 32. The needle 21 may be solid and have a sharpened end for piercing the patient's skin 11. Furthermore, the needle 21 may be made of a material that is more rigid than the cannula 23. In some embodiments, the needle 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient.

In some embodiments, the needle assembly 12 may include one or more springs (e.g., coil springs, torsion springs, etc.) initially retained in an energized state, and which are released upon depression of the actuator 28 in order to insert the needle 21 and cannula 23, or hollow needle, into the patient. Furthermore, retraction of the needle 21 may be achieved by the automatic release of another spring after the needle 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

The container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the needle assembly 12 inserts a delivery member such as the cannula 23 into the patient. This configuration may allow the on-body injector to have a generally planar, low-profile shape that can be worn by the patient without impeding the patient's movement. Initially, a stopper 34 or other piston member may be positioned in the reservoir 30 at a first end 36 of the container 14. The stopper 34 may sealingly and slidably engage the interior surface 43 of the wall 38 of the container 14, and may be movable relative to the wall 38 of the container 14.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 30 may be completely or partially filled with the drug 32. The drug 32 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may exert a force on the first end 36 of the container 14. For example, the drive mechanism 24 may push the stopper 34 along the longitudinal axis A from the first end 36 of the container 14 to a second end 37 of the container 14 in order to expel or urge the drug 32 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand or contract to move the stopper 34 through the reservoir 30 along the longitudinal axis A from the first end 36 of the container 14 to the second end 37 of the container 14. In other embodiments, the drive mechanism 24 may include an electric motor (not illustrated) which rotates a gear mechanism, including for example one or more sprocket gears, to cause axial motion of the stopper 34 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy. Other examples are possible.

The fluid pathway assembly 22 may be configured to establish fluid communication between the container 14 and the needle assembly 12 via a sterile fluid flow path during operation of the drug delivery device 10. The first end 44 of the fluid pathway assembly 22 may include the container access needle 60 and an overmold member 62. In general, the overmold member 62 may serve as a mounting member or connection hub for the container access needle 60 and provide a portion of the container access needle 60 which does not access the reservoir 30 with an enlarged outer dimension, such as an enlarged outer diameter. The container access needle 60 may have a sharpened end or point 63, corresponding to a first end of the container access needle 60, and a second end 64 in fluid communication with a fluid flow connection.

The fluid pathway assembly 22 may include a first end 44 connected to the second end 37 of the container 14, a second end 48 connected to a first end of the needle assembly 12, the fluid flow connection 50 extending between the first end 44 and the second end 48, and a backflow prevention mechanism 70 associated with at least one of the container 14, the fluid flow connection 50, or the needle assembly 12. In the illustrated example, the backflow prevention mechanism 70 is disposed within the fluid flow connection 50. As described in more detail below, in some embodiments the first end 44 of the fluid pathway assembly 22 may be connected to the container 14 via a clip member 53. The fluid flow connection 50 may be sterilized, and may be partially or entirely made of a flexible tubing 52 such as, for example, a polymer or other material. Initially, there may be slack in the flexible tubing 52 to allow the fluid pathway assembly 22 to move relative to the housing 29 and/or to allow components of the needle assembly 12, that the fluid pathway assembly 22 is attached thereto, to move relative to the housing 29. As illustrated in FIG. 2, the second end 48 of the fluid flow connection 50 may have a ball or plug 49 that may be inserted into a reservoir receptacle in the needle assembly 12 to create a seal between the fluid flow connection 50 and the needle assembly 12. As illustrated in FIGS. 2, 3A and 3B, the ball or plug 49 may be positioned at the second end 48 of the fluid flow connection 50. Further, as illustrated in FIGS. 2 and 3B, the plug 49 may include an opening or bore 49a that allows the fluid flow connection 50 to pass through to create a complete fluid flow path to the needle assembly 12.

FIGS. 3A and 3B illustrate an example needle assembly (also referred to as an insertion mechanism) 120 that corresponds to the needle assembly 12 illustrated in FIGS. 1 and 2. The needle assembly 120 may be incorporated in a drug delivery device such as the drug delivery device 10 depicted in FIG. 1. The needle assembly 120 includes a needle hub 122, a needle or trocar 121 coupled to the needle hub 122, a boot 130 being removably coupled to the needle hub 122, a cannula 140 at least partially disposed within an interior volume 131 of the flexible boot 130, and a spring 150 coupled to the needle hub 122. The needle 121 may have a hollow interior to allow for the drug 32 to flow through. The needle assembly 120 may include any number of additional components and/or features to assist in operation. In some examples, delivery of the drug 32 may be delayed to a time after the needle assembly 120 inserts the needle 121 and or cannula 140 into the user. In some examples, drug delivery may occur either incrementally or as a bolus.

In these examples, and as illustrated in FIGS. 3A and 3B, the second end 48 of the fluid flow connection 50 is inserted in or coupled to the reservoir receptacle or opening 124 in the needle hub 122 at a coupling region 71. At the termination point of the fluid flow connection 50, the drug 32 enters the cannula 140 and flows through the hollow interior of the needle 121 to be delivered to a user.

As illustrated in FIGS. 2-4B, the backflow prevention mechanism 70 may be positioned, disposed, and/or coupled at a coupling region 71 where the fluid flow connection 50 is coupled to the needle assembly 12. In other examples, the backflow prevention mechanism 70 may be positioned at other locations within the device 10 along the flow path (such as, for example, at a location within the needle assembly 12). In an example, the backflow prevention mechanism 70 may be coupled to the needle hub 122 via a press fit connection. Other suitable approaches may be used to couple the backflow prevention mechanism 70 at the coupling region 71. The backflow prevention mechanism 70 may include at least one flow restrictor 72 that restricts a fluid from flowing from the needle assembly 12 toward the container 14 via the fluid flow connection 50.

Figure 5:
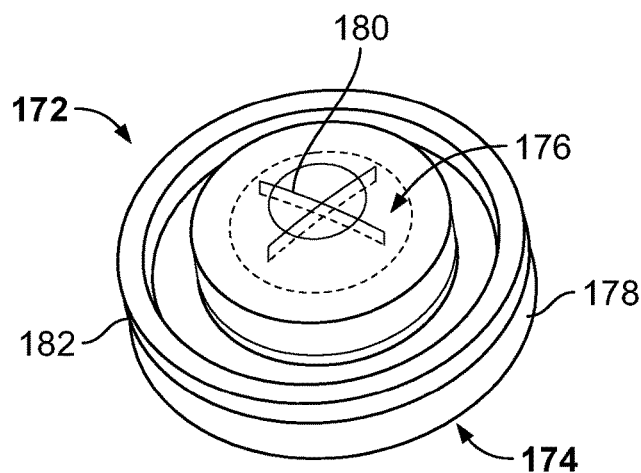
FIG. 5 illustrates a perspective view of a first example backflow prevention mechanism in the form of a slit valve in accordance with various embodiments.

FIG. 5 illustrates one example of a flow restrictor 172 corresponding to the flow restrictor 72 illustrated in FIGS. 4A and 4B. In the illustrated example, the flow restrictor 172 is in the form of a one-way slit valve having an inlet portion 174, an outlet portion 176, a valve body 178 extending between the inlet portion 174 and the outlet portion 176, and one or more slits or openings 180 defined by the valve body 178 to allow the drug 32 to pass therethrough. The flow restrictor 172 may also include a groove 182 to accommodate a corresponding protrusion (not shown) at the coupling region 71 to couple the flow restrictor 172 thereto. The flow restrictor 172 may be partially and/or entirely constructed from a resilient and/or flexible material such as a rubber and/or a polymeric material.

The flow restrictor 172 is positioned in the device 10 such that the inlet portion 174 is disposed upstream of the outlet portion 176. In other words, the inlet portion 174 of the flow restrictor 172 is disposed closer to the container 14; whereas the outlet portion 176 of the flow restrictor 172 is disposed closer to the needle assembly 12. So configured, when it is desired to deliver the drug 32 to a user, the device 10 is actuated, and the drug 32 flows from the container 14 along the fluid flow connection 50, through the inlet portion 174 of the flow restrictor 172, and through the outlet portion 176 of the flow restrictor 172 via the slits or openings 180.

In the illustrated example, the outlet portion 176 of the flow restrictor 172 opens at the slits 180 to allow the drug 32 to pass through to the needle assembly 12 to be delivered. Due to the inherent resilience of the flow restrictor 172, upon completion of delivery of the drug 32, the slits 180 will close and thus will restrict the drug 32 or other fluids from flowing from the outlet portion 176 of the flow restrictor 172 to the inlet portion 174 of the flow restrictor 172.

In some of these examples, it may be desired to prevent unintended forward flow. Environmental pressure changes due to altitude may cause the expansion of air bubbles in the container 14 or the fluid flow connection 50 of these devices. This expansion can urge drug out of the needle, thus resulting in unintended delivery. The use of one-way valves with cracking pressures that exceed naturally occurring pressure differentials can prevent these occurrences. Accordingly, the cracking pressure of the flow restrictor 172 may also be configured at greater than approximately 2 psi to prevent forward flow of air or medication when not desired.

Figure 6A:
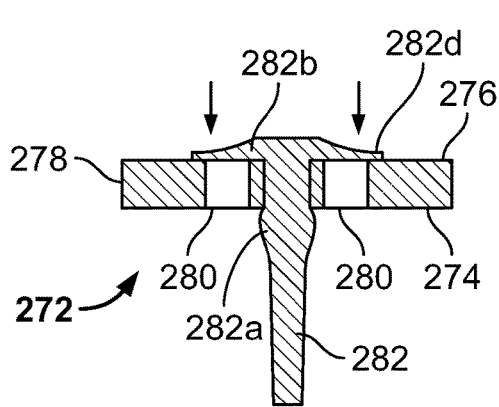
FIGS. 6A and 6B illustrate side cross-sectional views of a second example backflow prevention mechanism in the form of an umbrella valve in accordance with various embodiments.
Figure 6B:
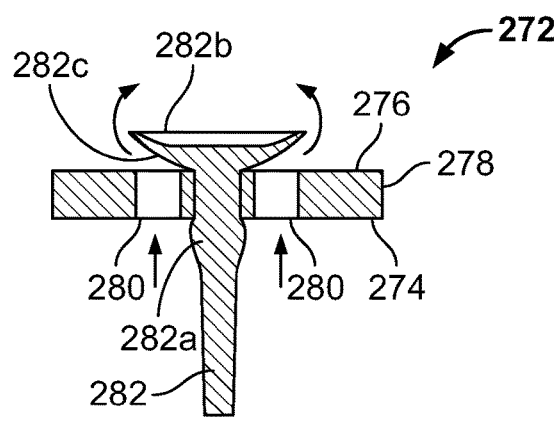

FIGS. 6A and 6B illustrate a second example of a flow restrictor 272 corresponding to the flow restrictor 72 illustrated in FIGS. 4A and 4B. In the illustrated example, the flow restrictor 272 is in the form of a one-way (normally-closed) umbrella valve having an inlet portion 274, an outlet portion 276, a valve body 278 extending between the inlet portion 274 and the outlet portion 276, and one or more openings 280 defined by the valve body 278 to allow the drug 32 to pass therethrough. The flow restrictor 272 also includes an umbrella member 282 operatively coupled to the valve body 278 using any number of suitable approaches (e.g., via a press-fit connection, a threaded connection, and the like). The flow restrictor 272 may also include a groove (not shown) or other coupling mechanisms used to couple the flow restrictor 272 at the coupling region 71.

The umbrella member 282 includes a base portion 282a and a flap portion 282b, and may be partially and/or entirely constructed from a resilient and/or flexible material such as a rubber and/or a polymeric material to allow for movement between the first and second configurations. Similarly, the valve body 278 may be partially and/or entirely constructed from a resilient and/or flexible material such as a rubber and/or a polymeric material.

The flap portion 282b of the umbrella member 282 includes a first surface 282c and a second surface 282d and is movable between a first, closed position (FIG. 6A) and a second, open position (FIG. 6B) to selectively cover the opening or openings 280. The flap portion 282b may include any number of support structures to assist in maintaining its shape and/or configuration. In some examples, the flap portion 282b is formed integrally with the base portion 282a, and in some examples, the flap portion 282b is a discrete component.

The flow restrictor 272 is positioned in the device 10 such that the inlet portion 274 is disposed upstream of the outlet portion 276. In other words, the inlet portion 274 of the flow restrictor 272 is disposed closer to the container 14; whereas the outlet portion 276 of the flow restrictor 272 is disposed closer to the needle assembly 12. So configured, and as illustrated in FIG. 6B, when it is desired to deliver the drug 32 to the patient, the device 10 is actuated, and the drug 32 flows from the container 14 along the fluid flow connection 50, through the inlet portion 274 of the flow restrictor 272, and through the outlet portion 276 of the flow restrictor 272 via opening or openings 280. The cracking pressure of the flow restrictor 272 may also be configured at greater than approximately 2 psi to prevent forward flow of air or medication when not desired.

With continued reference to FIG. 6B, upon flowing through the opening or openings 280, the drug 32 exerts pressure on the first surface 282c of the flap portion 282b, which in turn urges the flap portion 282b to the second, open position to allow the drug 32 to pass through to the needle assembly 12 (as denoted by the arrows in FIG. 6B) to be delivered. In some examples, the inherent resilience of the umbrella member 282 may cause the flap portion 282b to return to the closed configuration (FIG. 6A). In other examples, the flap portion 282b may maintain the open configuration until an opposing pressure is exerted thereon.

As illustrated in FIG. 6A, in the event that the drug 32 or other fluids flow in the opposite direction (e.g., from the outlet portion 276 of the flow restrictor 272 to the inlet portion 274 of the flow restrictor 272, the drug 32 or other fluid will contact the second surface 282d of the flap portion 282b, thereby causing the flap portion 282b to return to the closed configuration. Accordingly, and as denoted by the arrows in FIG. 6A, the flap portion 282b will restrict the drug 32 or other fluids from flowing through the opening or openings 280.

Figure 7A:
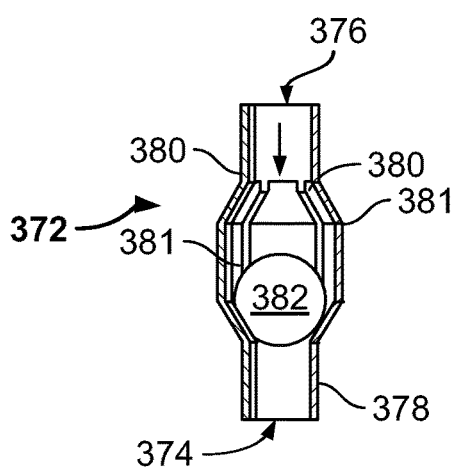
FIGS. 7A and 7B illustrate side cross-sectional views of a third example backflow prevention mechanism in the form of a ball valve in accordance with various embodiments.
Figure 7B:
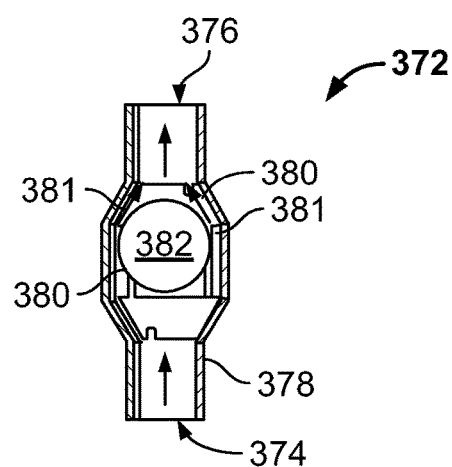

FIGS. 7A and 7B illustrate a third example of a flow restrictor 372 corresponding to the flow restrictor 72 illustrated in FIGS. 4A and 4B. In the illustrated example, the flow restrictor 372 is in the form of a one-way ball valve having an inlet portion 374, an outlet portion 376, a generally hollow valve body 378 extending between the inlet portion 374 and the outlet portion 376, and any number of elongated ledges 380 defined by the valve body 378 to form channels 381 that allow the drug 32 to pass from the inlet portion 374 to the outlet portion 376. The flow restrictor 372 also includes a ball member 382 disposed within the valve body 378 that is movable between a first, closed position (FIG. 7A) and a second, open position (FIG. 7B) to selectively restrict or permit fluid flow. The flow restrictor 372 may also include a groove (not shown) or other coupling mechanisms used to couple the flow restrictor 372 at the coupling region 71. The components of the flow restrictor 372 may be constructed from any number of suitable materials.

The ledge or ledges 380 in the valve body 378 at least partially extend into the outlet portion 376 of the valve body 378, but terminate prior to reaching the inlet portion 374 of the valve body 378. As a result, as illustrated in FIG. 7B, when the ball member 382 is positioned in the second, open position (FIG. 7B), the ball member 382 abuts the ledge or ledges 380, which maintains a gap to accommodate the channel 381, and thus flow is permitted from the inlet portion 374, through the flow channel or channels 381, and through the outlet portion 376. Conversely, when the ball member 382 is positioned in the first, closed position (FIG. 7A), the ball member 382 contacts the valve body 378 to create a seal, thereby restricting flow from the outlet portion 376 to the inlet portion 374.

The flow restrictor 372 is positioned in the device 10 such that the inlet portion 374 is disposed upstream of the outlet portion 376. In other words, the inlet portion 374 of the flow restrictor 372 is disposed closer to the container 14; whereas the outlet portion 376 of the flow restrictor 372 is disposed closer to the needle assembly 12. So configured, and as illustrated in FIG. 7B, when it is desired to deliver the drug 32 to a user, the device 10 is actuated, and the drug 32 flows from the container 14 along the fluid flow connection 50, and through the inlet portion 374 of the flow restrictor 372. Upon flowing through the inlet portion 374, the drug 32 exerts a pressure on the ball member 382 which causes it to move towards the outlet portion 376 in the second, open configuration that allows the drug 32 to pass through the channels 381 to the needle assembly 12 (as denoted by the arrows in FIG. 7B) to be delivered.

As illustrated in FIG. 7A, in the event that the drug 32 or other fluids flow in the opposite direction (e.g., from the outlet portion 376 of the flow restrictor 372 to the inlet portion 374 of the flow restrictor 372, the drug 32 or other fluid will contact and urge the ball member 382 towards the inlet portion 374 into the first, closed configuration. Accordingly, and as denoted by the arrows in FIG. 7A, the ball member 382 will seal against the valve body 378, preventing the drug 32 or other fluids from flowing back through the inlet portion 374.

FIGS. 8A-8D illustrate a fourth example of a flow restrictor 472 corresponding to the flow restrictor 72 illustrated in FIGS. 4A and 4B. In the illustrated example, the flow restrictor 472 is in the form of a one-way (normally-closed) duckbill valve having an inlet portion 474, an outlet portion 476, a generally hollow valve body 478 extending between the inlet portion 474 and the outlet portion 476 that defines an opening 480 that allows the drug 32 to pass from the inlet portion 474 to the outlet portion 476. The flow restrictor 472 also includes a duckbill member 482 disposed within and operatively coupled to the valve body 478 using any number of suitable approaches (e.g., via a press-fit connection, a threaded connection, and the like). The flow restrictor 472 may also include a protrusion 473, groove (not shown), or other coupling mechanisms used to couple the flow restrictor 472 at the coupling region 71. The components of the flow restrictor 472 may be constructed from any number of suitable materials such as, for example, rigid materials for the valve body 478, and resilient materials for the duckbill member 482.

The duckbill member 482 includes a base portion 482a and a flap portion 482b. The flap portion 482 includes an interior surface 482c and an exterior surface 482d. Further, an outlet portion 484 is disposed at or near the downstream end of the flap portion 482b. In some examples, the flap portion 482b is formed integrally with the base portion 482a, and in some examples, the flap portion 482b is a discrete component. The duckbill member 482 may be partially and/or entirely constructed from a resilient and/or flexible material such as a rubber and/or polymeric material.

Figure 8B:
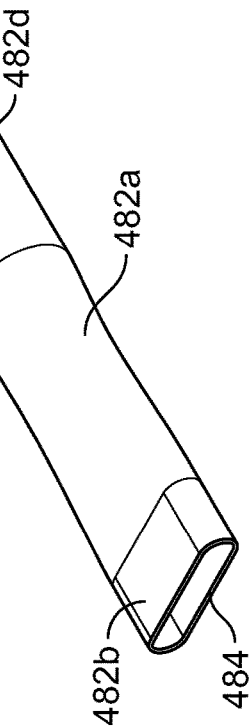
FIGS. 8A and 8B illustrate side cross-sectional views of a fourth example backflow prevention mechanism in the form of a duckbill valve in accordance with various embodiments.
Figure 8D:
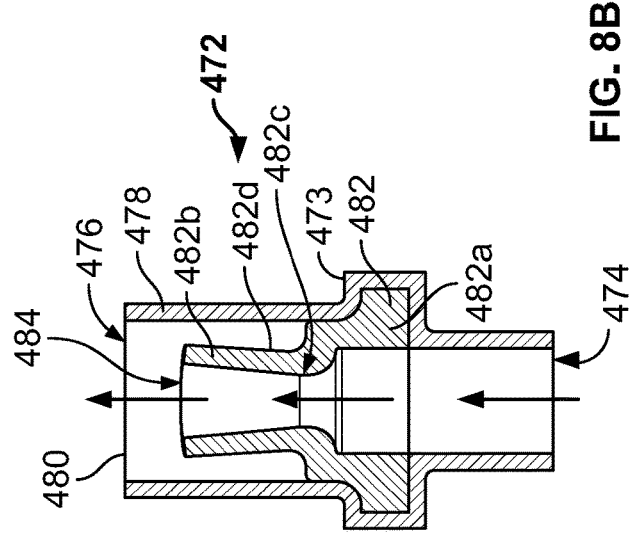
FIGS. 8C and 8D illustrated perspective views of the fourth example backflow prevention mechanism of FIGS. 8A and 8B in accordance with various embodiments.

The duckbill member 482 is movable between a first, closed position (FIGS. 8A and 8C) and a second, open position (FIGS. 8B and 8D). The duckbill member 482 remains in the first, closed position until the pressure differential across the flow restrictor 472 (the difference between the pressure in the inlet portion 474 and the outlet portion 476) exceeds the valve cracking pressure. When the duckbill member 482 is in the first, closed position, the interior surfaces 482c of the flap portion 482b contact each other, forming a seal at the outlet portion 484. When the pressure differential across the flow restrictor 472 exceeds the cracking pressure, the duckbill member moves to the second, open position and the interior surfaces 482c of the flap portion 482b move apart, forming an opening at the outlet portion 484.

The flow restrictor 472 is positioned in the device 10 such that the inlet portion 474 is disposed upstream of the outlet portion 476. In other words, the inlet portion 474 of the flow restrictor 472 is disposed closer to the container 14; whereas the outlet portion 476 of the flow restrictor 472 is disposed closer to the needle assembly 12. So configured, and as illustrated in FIGS. 8B and 8D, when it is desired to deliver the drug 32 to a user, the device 10 is actuated, and the drug 32 flows from the container 14, along the fluid flow connection 50, through the inlet portion 474 of the flow restrictor 472, to the flap portion 482b of the duckbill member 482. The drug 32 then exerts pressure against the interior surfaces 482c of the flap portion 482b, which causes the duckbill member 482 to move to the second, open position, expanding the outlet portion 484 of the duckbill member 482 allowing the drug 32 to pass through the outlet portion 476 of the flow restrictor 472 (as denoted by the arrows in FIG. 8B) to be delivered. Whenever the pressure differential across the flow restrictor 472 is less than the cracking pressure, the inherent resilience of the duckbill member 482 causes it to return to the first, closed position closing the outlet portion 484 of the duckbill member 482 and forming a seal. The cracking pressure of the flow restrictor 472 may be configured to be approximately 2 psi (or greater) to prevent forward flow of air or medication when not desired.

Figure 8A:
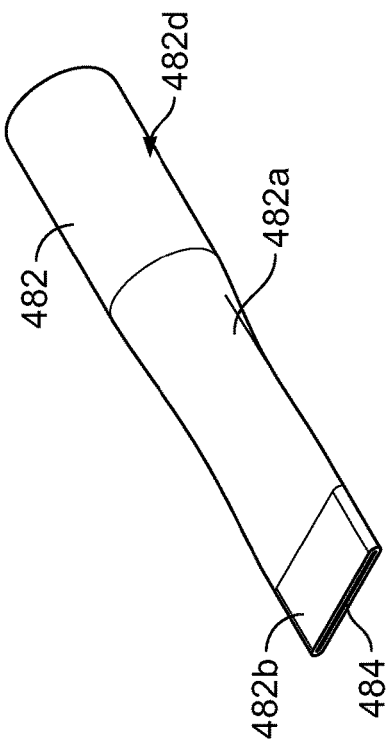
Figure 8C:
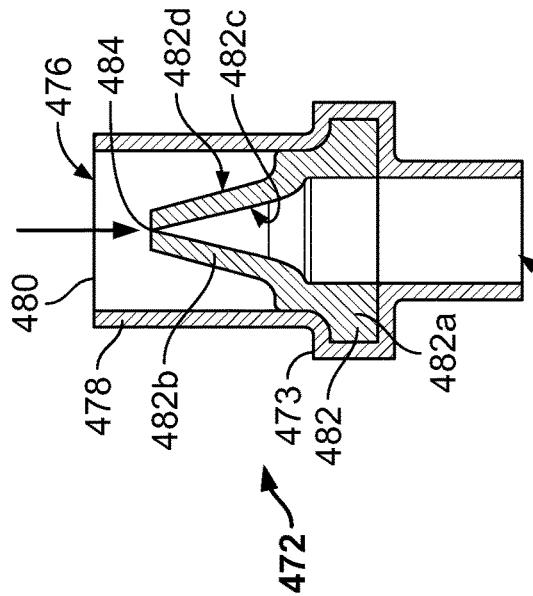

As illustrated in FIG. 8A, in the event that the drug 32 or other fluids flow in the opposite direction (e.g., from the outlet portion 476 of the flow restrictor 472 to the inlet portion 474 of the flow restrictor 472), the drug 32 or other fluid will contact the outer surface 482d of the flap portion 482b of the duckbill member 282. Accordingly, and as denoted by the arrows in FIG. 8A, the duckbill member 482 will restrict the drug 32 or other fluids from flowing back through the outlet portion 476 to the inlet portion 474.

FIGS. 9A and 9B illustrate a fifth example of a flow restrictor 572 corresponding to the flow restrictor 72 illustrated in FIGS. 4A and 4B. In the illustrated example, the flow restrictor 572 is in the form of a one-way flap, plate, or diaphragm valve having an inlet portion 574, an outlet portion 576, a generally hollow valve body 578 extending between the inlet portion 574 and the outlet portion 576, and a cap member 579 having one or more openings 579a in fluid communication with the valve body 578. The valve body 578 includes any number of ledges 580 defined by the valve body 578 to form channels 581 that allow the drug 32 to pass from the inlet portion 574 to the outlet portion 576. In some examples, the cap member 579 is integrally formed with the ledges 580. The flow restrictor 572 also includes a flap, plate, and/or diaphragm member 582 disposed within the cap member 579 that is movable between an open position (FIG. 9A) and a closed position (FIG. 9B) to selectively permit or restrict fluid flow. The flow restrictor 572 may also include a groove (not shown) or other coupling mechanisms used to couple the flow restrictor 572 at the coupling region 71. The components of the flow restrictor 572 may be constructed from any number of suitable materials.

The ledge or ledges 580 in the valve body 578 at least partially extend into the outlet portion 576 of the valve body 578. The flap member 582 is movable between an upper surface 580a of the ledge or ledges 580 and an inner surface 579b of the cap member 579. As illustrated in FIG. 9A, when the flap member 582 is positioned against the upper surface 580a of the ledge or ledges 580, fluid may flow from the inlet portion 574, through the cap member opening 579a, through the channels 581 to the outlet portion 576. In some examples, the outer diameter of the flap member 582 may be smaller than the inner diameter of the cap 579, and thus fluid may flow to the outlet portion 576. Conversely, when the flap member 582 is positioned in the closed position (FIG. 9B), the flap member 582 contacts the inner surface 579b of the cap member 579 to create a seal, thereby restricting flow from the outlet portion 576 to the inlet portion 574.

The flow restrictor 572 is positioned in the device 10 such that the inlet portion 574 is disposed upstream of the outlet portion 576. In other words, the inlet portion 574 of the flow restrictor 572 is disposed closer to the container 14; whereas the outlet portion 576 of the flow restrictor 572 is disposed closer to the needle assembly 12. So configured, and as illustrated in FIG. 9A, when it is desired to deliver the drug 32 to a user, the device 10 is actuated, and the drug 32 flows from the container 14 along the fluid flow connection 50, and through the inlet portion 574 of the flow restrictor 572. Upon flowing through the inlet portion 574, the drug 32 exerts a pressure on the flap member 582 which causes it to move towards the outlet portion 576 and rest on the upper surface 580a of the ledge or ledges 580 in the open configuration that allows the drug 32 to pass through the channels 581 to the needle assembly 12 (as denoted by the arrows in FIG. 9A) to be delivered.

As illustrated in FIG. 9B, in the event that the drug 32 or other fluids flow in the opposite direction (e.g., from the outlet portion 576 of the flow restrictor 572 to the inlet portion 574 of the flow restrictor 572), the drug 32 or other fluid will contact and urge the flap member 582 towards the inner surface 579b of the cap member 579 and thus into the closed configuration where the flap member 582 seals the opening 579a of the cap member 579. Accordingly, and as denoted by the arrows in FIG. 9B, the flap member 582 will restrict the drug 32 or other fluids from flowing back through the opening 579a of the cap member 579 and the inlet portion 574.

FIGS. 10A-10C illustrate a sixth example of a flow restrictor 672 corresponding to the flow restrictor 72 illustrated in FIGS. 4A and 4B. The flow restrictor 672 is in the form of an alternate one-way flap, plate, or diaphragm valve having similar features as the flow restrictor 572 illustrated in FIGS. 9A and 9B. Accordingly, features in the flow restrictor 672 having identical two-digit suffixes as those illustrated in the flow restrictor 572 of FIGS. 9A and 9B will not be discussed for the sake of brevity.

The flow restrictor 672 additionally includes a protruding member 685 positioned within the valve body 678. In the illustrated example of FIG. 10A, in a first, open (resting) configuration, the flap member 682 abuts the protruding member 685. In this configuration, the channels 681 allow fluid to flow between the inlet portion 674 and the outlet portion 676. In a second, flexed configuration as illustrated in FIG. 10B, pressure exerted on the flap member 682 by the drug 32 causes the flap member to flex towards the outlet portion 676 to provide for full fluid flow through the flow restrictor 672. As illustrated in FIG. 10C, in the event that the drug 32 or other fluids attempt to flow in the opposite direction (e.g., from the outlet portion 676 to the inlet portion 674), the flap member 682 moves to abut against the inner surface 679b of the cap member 679 to seal the opening 679a. Accordingly, and as denoted by the arrows in FIG. 10C, the flap member 682 will restrict the drug 32 or other fluids from flowing back through the opening 679a of the cap member 679 and the inlet portion 674.

Figure 11A:
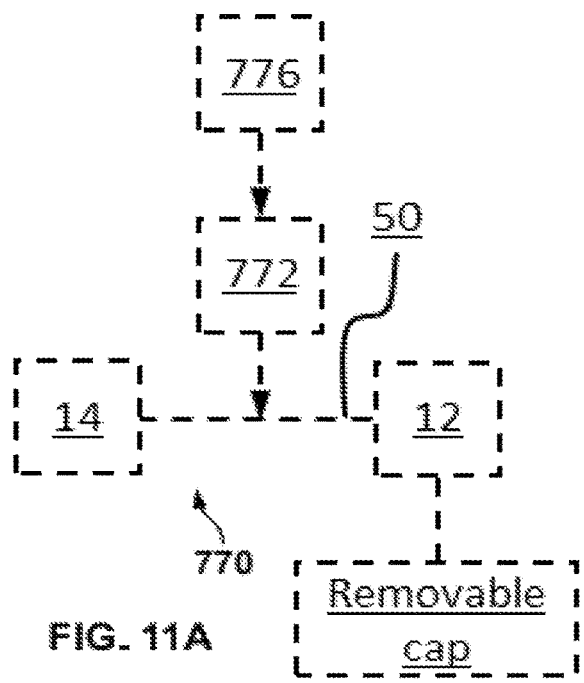
FIGS. 11A and 11B illustrate perspective and side cross-sectional views, respectively, of a seventh alternate backflow prevention mechanism using air exclusion in accordance with various embodiments.
Figure 11B:
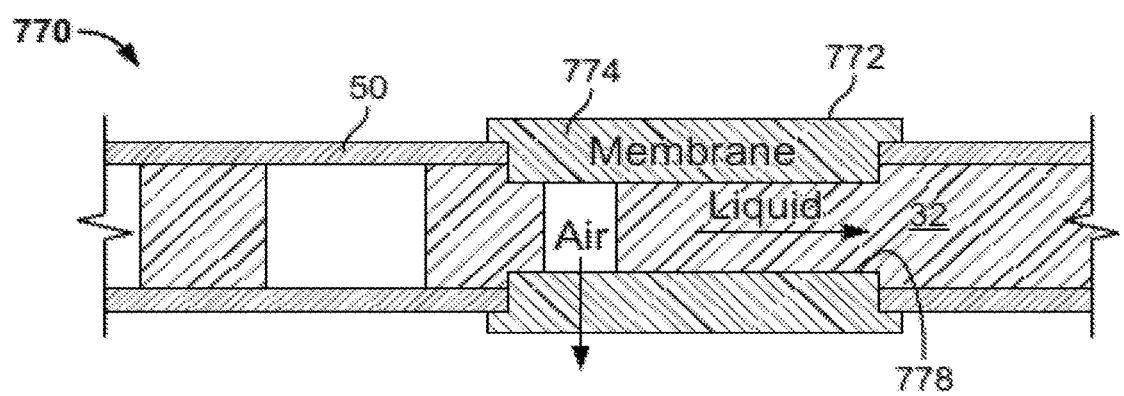

FIGS. 11A and 11B illustrate a seventh example of a backflow prevention mechanism 770, in the form of an air exclusion device 772 corresponding to the backflow prevention mechanism 70. In some cases, when the container 14 is filled with drug 32 via a fill port 776, air may be introduced into the fluid path (container 14, fluid pathway assembly 22, and/or fluid flow path 50), increasing the fluid path compliance as compared to an air-free/bubble-free fluid path. In the case of delayed delivery, this added compliance may allow blood or other fluids to enter the needle assembly 12, fluid flow path 50 or container 14 (backflow), increasing the likelihood of clots forming in the fluid path. Removal of air entrained during the filling process can assist in preventing clots in the device fluid path 50. To accomplish this, the air exclusion device 772 includes a debubbling membrane or filter plate 774 coupled to the fluid flow path 50 using any suitable approach such as, for example, a press-fit connection, a threaded connection, clamps, and/or other couplings.

Figure 12:
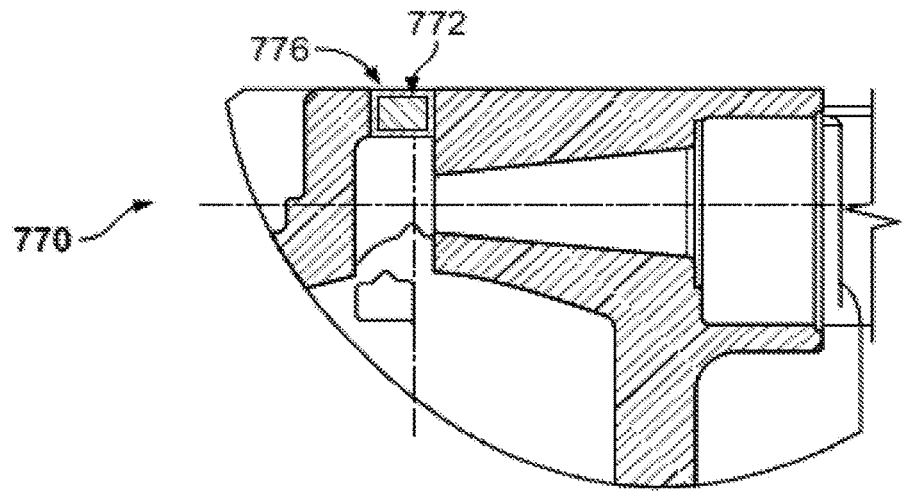
FIG. 12 illustrates a side cross-sectional view of an alternate placement of an example backflow prevention mechanism using air exclusion in accordance with various embodiments.

The debubbling membrane 774 may be constructed from a hydrophobic material such as microporous PTFE. Other suitable materials may additionally be used. In some examples, the debubbling membrane 774 may be disposed at or near a fill port 776 of the device 10 to remove air during the filling process. In these examples, and as illustrated in FIG. 11A, the air exclusion device 772 is disposed in the fluid flow path 50 at a position that is downstream (relative to the flow during the filling process) of the fill port 776. In other examples, and as illustrated in FIG. 12, the air exclusion device 772 is disposed within the fill port 776 of the device. Other locations are possible. In some examples, using a bubble-free prefilled syringe (not shown) may also assist in eliminating and/or reducing the amount of air introduced into the fluid path during the filling process. Further, in some examples, a removable cap or seal may be used to assist with the process of filling the device with the drug. Specifically, the removable cap would restrict the drug from flowing out of the needle assembly 12 during filling of the primary container 14.

In other examples, and as illustrated in FIG. 11B, the air exclusion device 772 may be formed by drilling a channel (e.g., a micro channel) 778 through the filter plate 774 to allow air bubbles pass through the filter plate 774 in any radial direction. In some examples, the flow rate during filling of the container 14 with the drug 32 is reduced using any number of flow restrictors (not shown) to allow more air to escape through the air exclusion device 7872. The presence of a large fluidic resistance downstream of the air exclusion device 772 increases the pressure inside the air exclusion device 772 during filling. This elevated pressure facilitates the passage of air through the filter plate 774 to the environment, thereby reducing the amount of air introduced into the fluid path during the filling process.

During the filling process, as the drug 32 flows through the filling port 776 and enters the air exclusion device 772, the pressure differential between the interior of the air exclusion device and the environment causes the entrained air to be expelled through the debubbling membrane 774, while the drug 32 continues to flow through the fluid flow path 50 to the container 14. The air exclusion device 772 may be used in conjunction with any number of additional backflow prevention mechanisms 70 described herein.

The efficiency of the air exclusion device 772 may depend on the ratio between liquid flow and gas flow. In some examples, the maximum removable bubble size for a given liquid flow rate may be determined if the air flow resistance of the filter plate 774 is known. In some examples, the channel 778 may have a diameter of approximately 0.25 mm and a length of approximately 5 mm, thus yielding a channel volume of approximately 0.25 µL. This design for the channel 778 results in an air exclusion device 772 having a low (sub-microliter) interior volume, which is desirable to minimize the quantity of drug 32 that is not delivered to the patient, while providing high air exclusion efficiency and high flow rates during filling of the container 14. Further, in some examples, the air exclusion device 772 may further include a hydrophilic element (not shown) that prevents entrained air from exiting the air exclusion device 772 via the liquid stream.

FIGS. 13A-13F illustrate an eighth example of a flow restrictor 872 corresponding to the flow restrictor 72 illustrated in FIGS. 4A and 4B. In the illustrated example, the flow restrictor 872 is in the form of a clamp valve 873 that is positioned at a lower portion of the needle assembly 120 where the needle 121 and cannula 140 project through an opening thereof to be inserted into a patient's tissue, though other locations are possible. The clamp valve 873 has a clamping mechanism 874 that includes any number of moveable elements or jaws 875 that communicate with the cannula 140 or other portion of the fluid flow connection 50, any number of pivot members 876, a resilient member 878, and a drive mechanism or actuator 880. Each jaw 875 includes a first end 875a, a second end 875b, a length 875c extending between the first and second ends 875a, 875b, and contact surface 875d that is positioned adjacent to the cannula 140 (or other portion of the fluid flow connection 50). Further, one or both jaws 875 includes a stop 875e that defines and limits a minimum aperture of the clamp to prevent damage (i.e., excessive compression) to the cannula 140. The pivot members 876 are positioned along the length 875c, and in some examples may be in the form of integral protrusions formed along the length 875c that rotatably couple to the needle assembly 120. In other examples, the pivot members 876 may be in the form of posts or protrusions that extend from the needle assembly 120 that insert into an opening or hole formed along the length 875c of the jaw 875. Other examples are possible.

The actuator 880 is positioned at or near the first end 875a of the jaw 875, and is configured to cause the jaw 875 to rotate about the pivot member 876. In some examples, the actuator 880 may be in the form of a pulley mechanism that generates relative movement of the jaw 875. Other actuator mechanisms, such as magnetic mechanisms, gear mechanisms, and the like may be used. The resilient member 878 is positioned at or near the second end 875b of the jaw 875, and is configured to exert a force that opposes the force exerted by the actuator 880 (depending on the configuration of the clamping mechanism being normally-open (as illustrated in FIGS. 13A-13C) or normally-closed (as illustrated in FIGS. 13D-13F)).

Figure 13A:
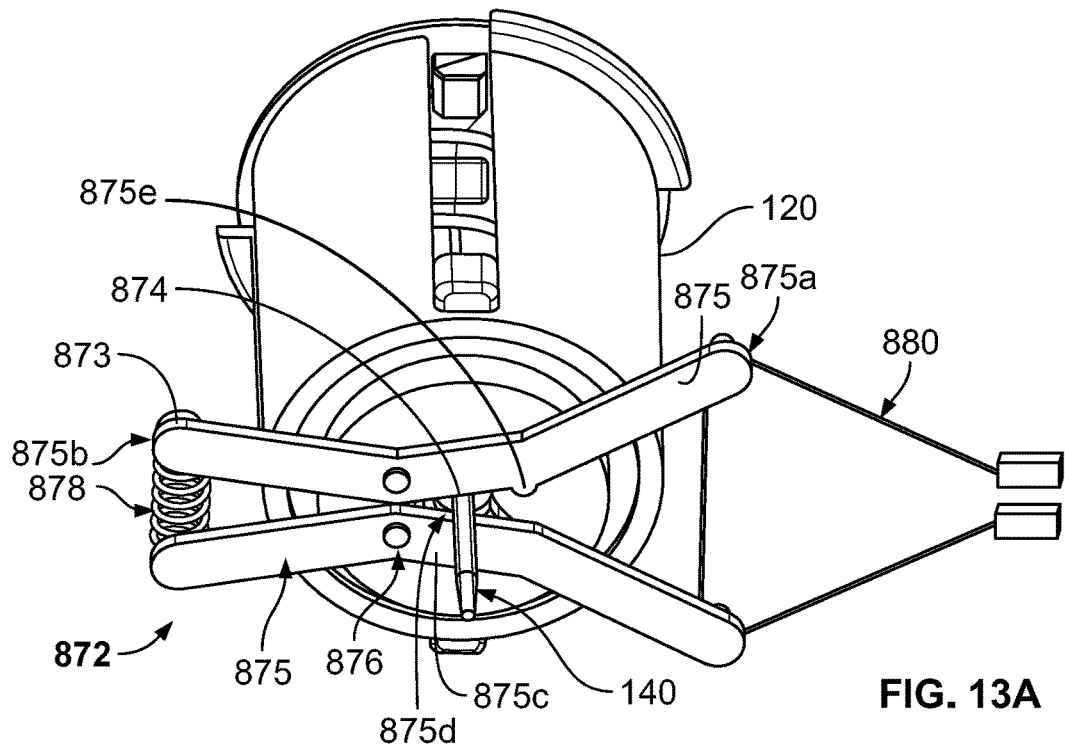
FIGS. 13A-13C illustrate perspective and rear elevation views, respectively, of an eighth alternate backflow prevention mechanism using a normally-open clamp assembly in accordance with various embodiments.
Figure 13B:
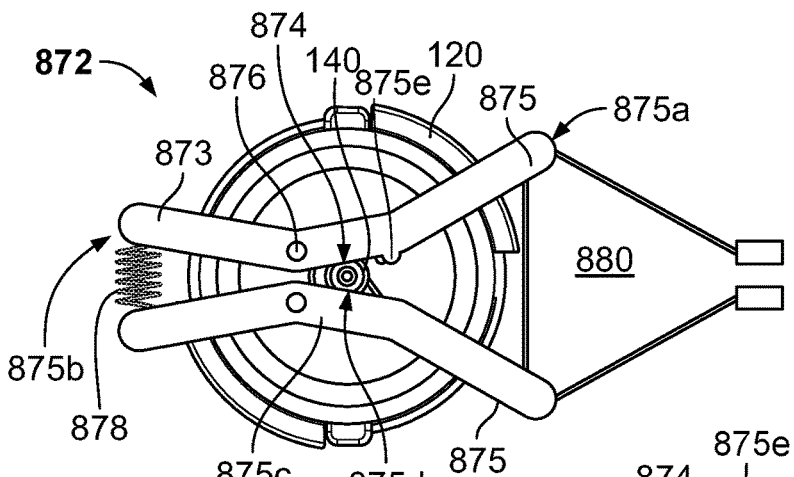
Figure 13C:
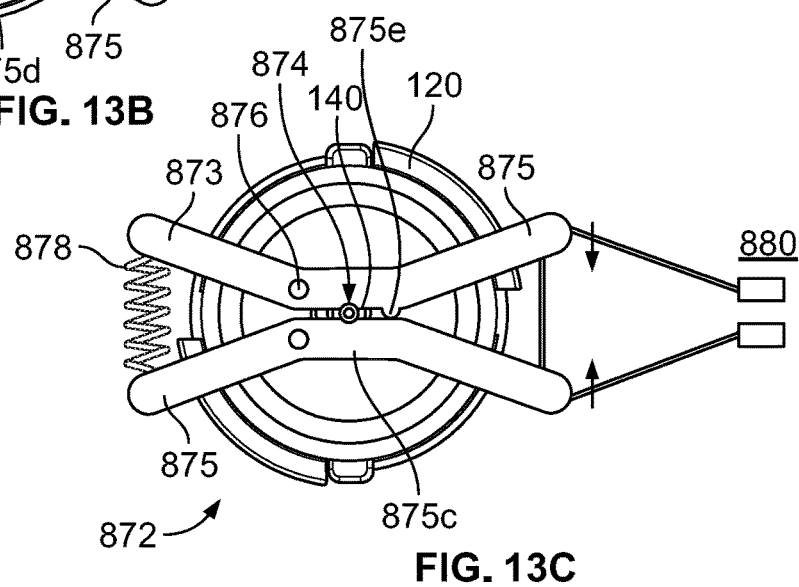

Specifically, as illustrated in FIGS. 13A-13C, a normally-open clamp valve 873 is provided whereby the resilient member 878 exerts a force on the jaws 875 to position them in an open configuration where fluid is permitted to flow out of the cannula 140 and/or the fluid flow connection 50 (as illustrated in FIGS. 13A and 13B). As shown in FIG. 13C, upon actuation of the actuator 880, the actuator 880 exerts a clamping force on the jaws 875 that is greater than the force exerted by the resilient member 878. As a result, the jaws 875 rotate about the pivot member 876 and squeeze or clamp the cannula 140 and/or the fluid flow connection 50 at the contact surface 875d of the jaws 875, thus restricting fluid flow in either direction. As an example, when a delay prior to drug delivery is desired, the actuator 880 may cause the clamping mechanism 874 to move to the closed configuration. When it is desired to administer the drug 32, the actuator 880 may stop exerting a force on the jaws 875, thus allowing the resilient member 878 to move the jaws 875 to the open configuration.

Figure 13D:
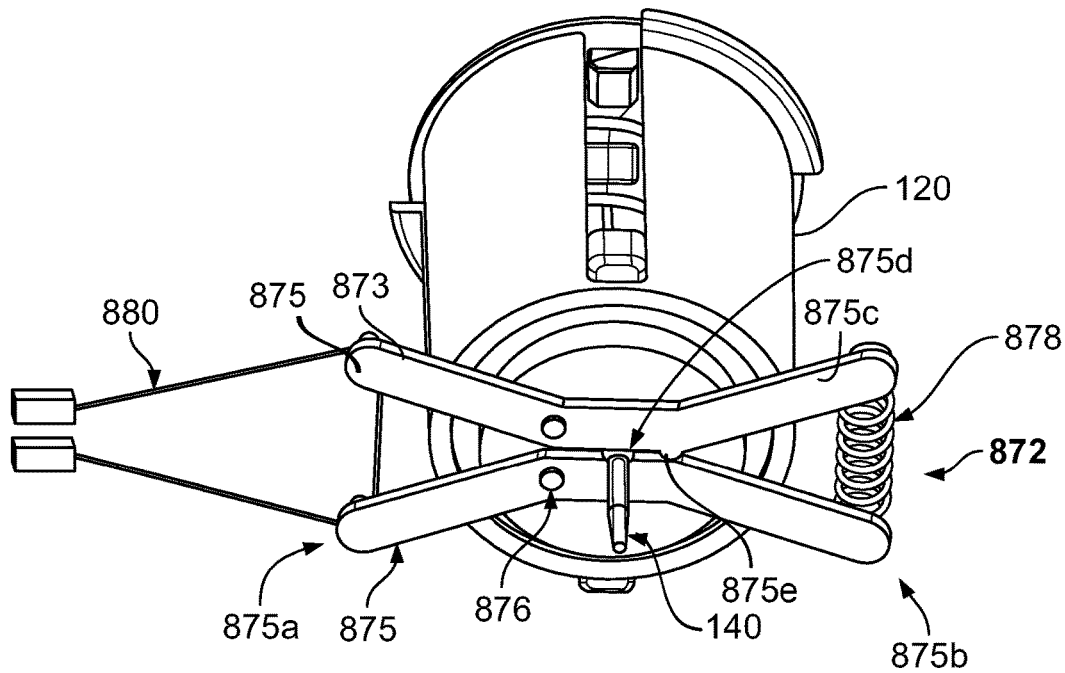
FIGS. 13D-13F illustrate perspective and rear elevation views, respectively, of the eighth alternate backflow prevention mechanism using a normally-closed clamp assembly in accordance with various embodiments.
Figure 13E:
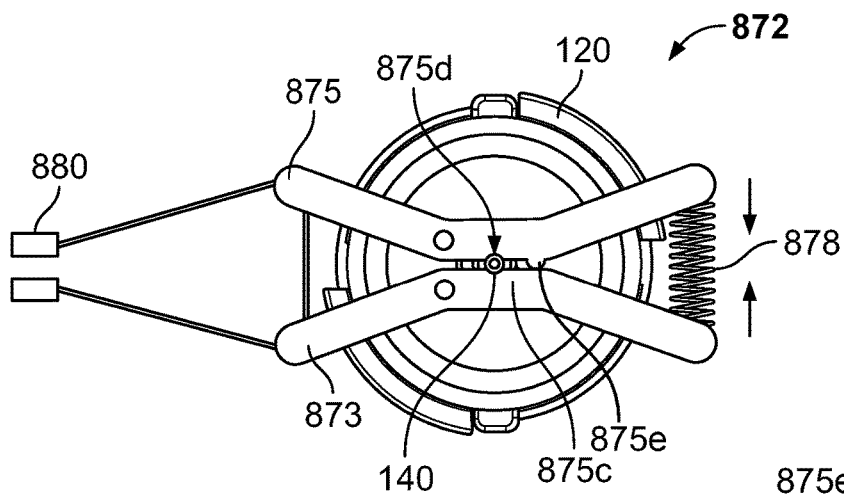
Figure 13F:
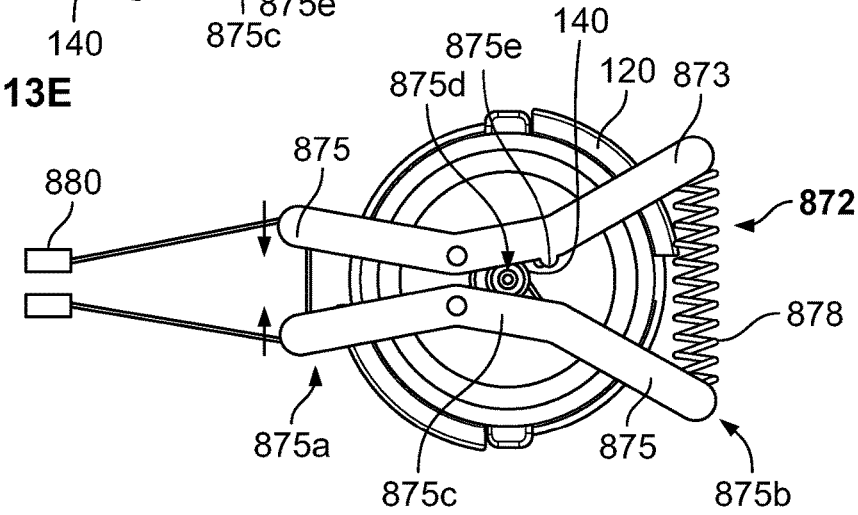

Turning to FIGS. 13D-13F, a normally-closed clamp valve 873 is provided whereby the resilient member 878 exerts a force on the jaws 875 to position them in a closed configuration where fluid is restricted from flowing through the cannula 140 and/or the fluid flow connection 50 in either direction (see FIGS. 13D and 13E). As shown in FIG. 13F, upon actuation of the actuator 880, the actuator 880 exerts a clamping force on the jaws 875 that is greater than the force exerted by the resilient member 878. As a result, the jaws 875 rotate about the pivot member 876 and are removed from gripping or clamping the cannula 140 and/or the fluid flow connection 50 at the contact surface 875d, thus permitting fluid flow in either direction, specifically to allow the drug 32 to be delivered to a patient. As an example, when a delay prior to drug delivery is desired, the actuator 880 does not exert a force on the jaws 875, and thus the clamping mechanism 874 are positioned in the closed configuration. When it is desired to administer the drug 32, the actuator 880 may exert a force on the jaws 875, thus overcoming the force exerted by the resilient member 878 to move the jaws 875 to the open configuration.

FIGS. 14A-14C illustrate a ninth example of a flow restrictor 972 corresponding to the flow restrictor 72 illustrated in FIGS. 4A and 4B. In the illustrated example, the flow restrictor 972 is in the form of a one-way (normally-closed) sleeve valve 973 having an inlet portion and an outlet portion that is positioned at or near the distal end of the needle 921. In this example, the sleeve valve 973 includes a rigid, hollow needle 921 having at least one side fluid port 921a that connects the inlet portion to the outlet portion, a flexible sleeve member 974 and a needle tip closure member 976. The flexible sleeve 974 is dimensioned to at least partially surround and/or encapsulate the outer diameter of the needle 921, and may be operatively coupled to the needle 921 using any number of suitable approaches (e.g., via an interference connection, an adhesive connection, and the like). The needle tip closure member 976 has an outer diameter equal to or greater than that of the flexible sleeve 974. In the present example, the needle tip closure member 976 is an accessory device attached to the needle 921. In alternate examples, the needle tip closure 976 may be formed integrally as a feature of the needle 921. The needle 921 may be equipped with any number of side fluid ports 921a to adjust fluidic resistance and drug injection time. The components of the flow restrictor 972 may be constructed from any number of suitable materials such as, for example, rigid materials for the needle 921 and tip closure member 976, and resilient materials for the flexible sleeve member 974.

The flexible sleeve 974 is movable between a first, closed position (FIGS. 14A and 14B) and a second, open position (FIG. 14C). The flexible sleeve 974 remains in the first, closed position until the pressure differential across the flow restrictor 972 (the difference between the pressure in the inlet portion and the outlet portion) exceeds the valve cracking pressure. When the flow restrictor 972 is in the first, closed position, the interior surface of the flexible sleeve member 974 covers and seals the side fluid port(s) 921a. During insertion of the needle 921 by the needle assembly 120, because the needle tip closure member 976 is dimensioned to have an outer diameter that is equal to or greater than that of the flexible sleeve 974, the needle tip closure member 976 prevents the leading edge of the flexible sleeve 974 from catching on the patient's tissue during needle insertion. When the pressure differential across the flow restrictor 972 exceeds the cracking pressure, the flexible sleeve member 974 moves to the second, open position and the interior surface of the flexible sleeve member 974 moves away from the exterior surface of the needle 921, exposing the fluid side port 921a.

The flow restrictor 972 is positioned in the device 10 such that the inlet portion is disposed upstream of the outlet portion. In other words, the inlet portion of the flow restrictor 972 is disposed closer to the container 14; whereas the outlet portion of the flow restrictor 972 is disposed closer to the needle assembly 12. So configured, and as illustrated in FIG. 14C, when it is desired to deliver the drug 32 to a patient, the device 10 is actuated and the drug 32 flows from the container 14, along the fluid flow connection 50, to the needle 921, through the inlet portion of the flow restrictor 972, through the fluid side port 921a until it contacts the interior surface of the flexible sleeve member 974. The drug 32 then exerts pressure against the interior surface of the flexible sleeve member 974, which causes the flexible sleeve member 974 to move to the second, open position, exposing the fluid side port 921a and allowing the drug 32 to be delivered (as denoted by the arrows in FIG. 8B). Whenever the pressure differential across the flow restrictor 972 is less than the cracking pressure, the inherent resilience of the flexible sleeve member 974 causes it to return to the first, closed position, covering the fluid side port 921a of the needle 921 and forming a seal. Accordingly, the flow restrictor 972 is self-closing after each increment or bolus of drug 32 is delivered. The cracking pressure of the flow restrictor 972 may be configured to be approximately 2 psi (or greater) to prevent forward flow of air or medication when not desired.

As illustrated in FIG. 14B, in the event that the drug 32 or other fluids flow in the opposite direction (e.g., from the outlet portion of the flow restrictor 972 to the inlet portion of the flow restrictor 972), the drug 32 or other fluid will contact the outer surface of the flexible sleeve member 974. Accordingly, and as denoted by the arrows in FIG. 14A, the flexible sleeve member 974 will restrict the drug 32 or other fluids from flowing back through the outlet portion to the inlet portion.

FIGS. 15A-15H illustrate a tenth example of a flow restrictor 1072 corresponding to the flow restrictor 72 illustrated in FIGS. 4A and 4B. In the illustrated example, the flow restrictor 1072 is in the form of an integrated sliding sleeve valve that is positioned at a lower portion of the needle assembly 120, and specifically, around a portion of the needle 1021. In this example, the flow restrictor 1072 includes a rigid needle 1021 and a soft cannula 1040 having a valve chamber 1074. The needle 1021 includes at least one fluid port 1021a, and has a closed tip portion. In these examples, the needle 1021 and the cannula 1040 are coupled together via a frictional, interference fit that covers the fluid port 1021a during any delay prior to drug delivery. In other words, the cannula 1040 prevents blood or other fluids from entering the needle 1021. In some examples, the clearance between the outside diameter of the needle 1021 and the inside diameter of the cannula 1040 is dimensioned to provide complete sealing of the fluid port 1021a while allowing smooth movement of the needle 1021 inside the cannula 1040.

As illustrated in FIG. 15A, the needle 1021 is used to insert the cannula 1040 through the skin 11 and into the subcutaneous tissue 13. After the cannula 1040 is inserted into the subcutaneous tissue 13, the needle is retracted to a "valve closed" position where its fluid port 1021a is sealed by the inside surface of the cannula, restricting fluid flow in either direction. In some examples, the needle 1021 may be left in this state to provide additional rigidity to the cannula 1040 in order to prevent kinking due to relative movement of the patient and the device during any delay prior to drug delivery. Such kinking may compromise delivery by either occluding or causing the cannula 1040 to withdraw from the skin 11 or subcutaneous tissue 13, resulting in the delivery of the drug 32 at the incorrect location/depth (e.g., on the skin 11 as opposed to at a specific depth within the subcutaneous tissue 13).

Figure 15C:
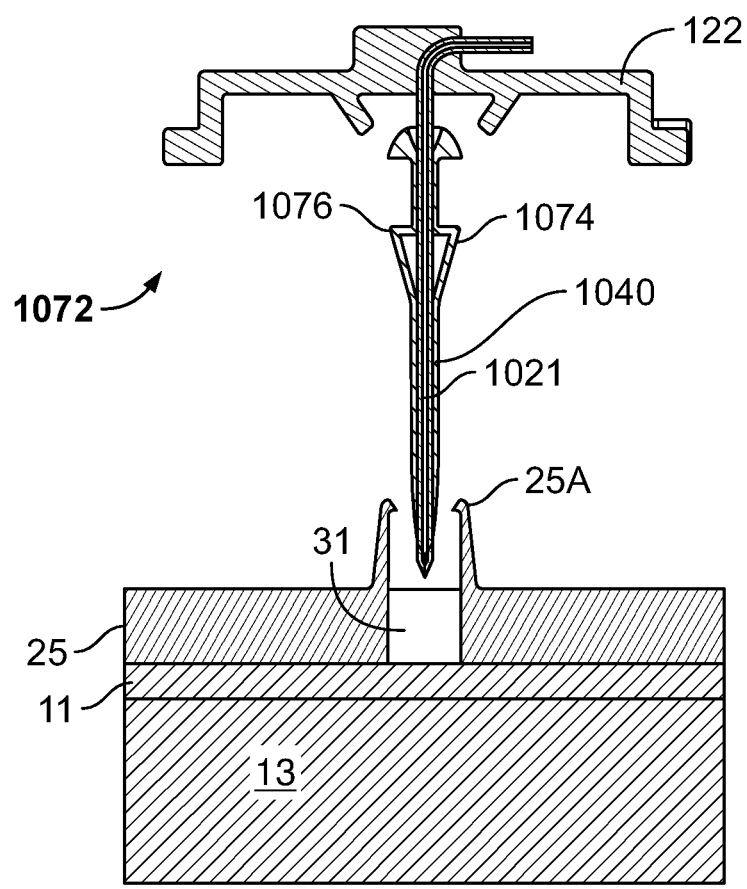
Figure 15D:
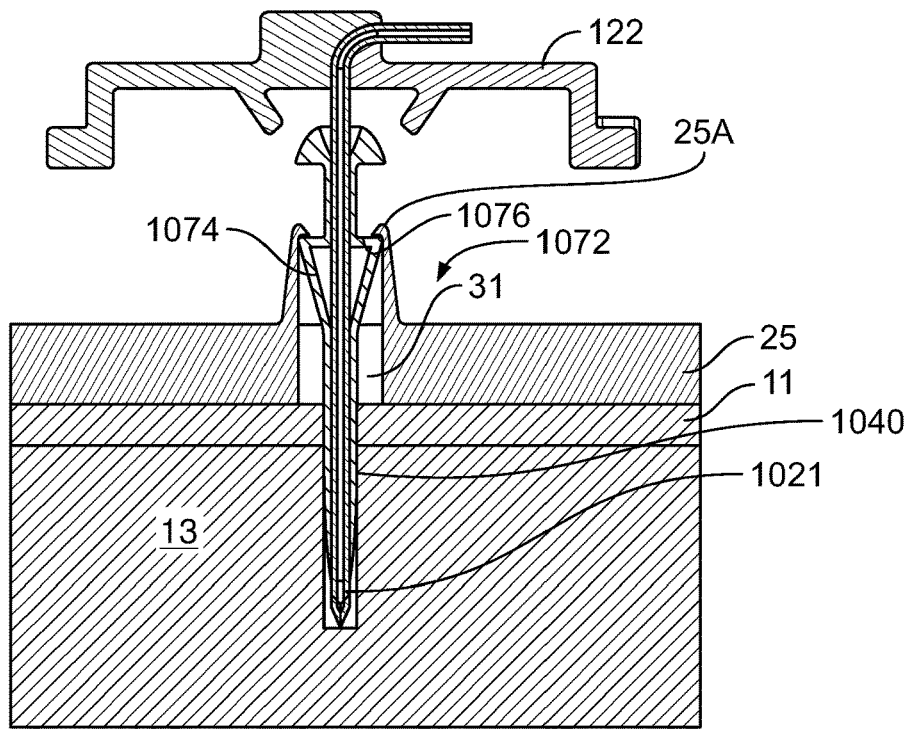

As illustrated in FIG. 15B, when desired, the needle 1021 may be moved to a "valve open" position where the fluid port 1021a is within the cannula valve chamber 1074. The drug 32 may then be delivered to the patient either incrementally or as a bolus. More specifically, as illustrated in FIG. 15C, in the initial, pre-activated state, both the needle 1021 and the cannula 1040 are positioned above the patient's skin 11. As illustrated in FIG. 15D, when the needle assembly 120 is activated, the needle 1021 and the cannula 1040 are inserted into the skin 11 and the subcutaneous tissue 13. The cannula 1040 includes a latching ledge 1076 that couples to any number of tabs 25a disposed on the bottom wall 25 of the device 10 to secure the cannula 1040 in place.

Figure 15E:
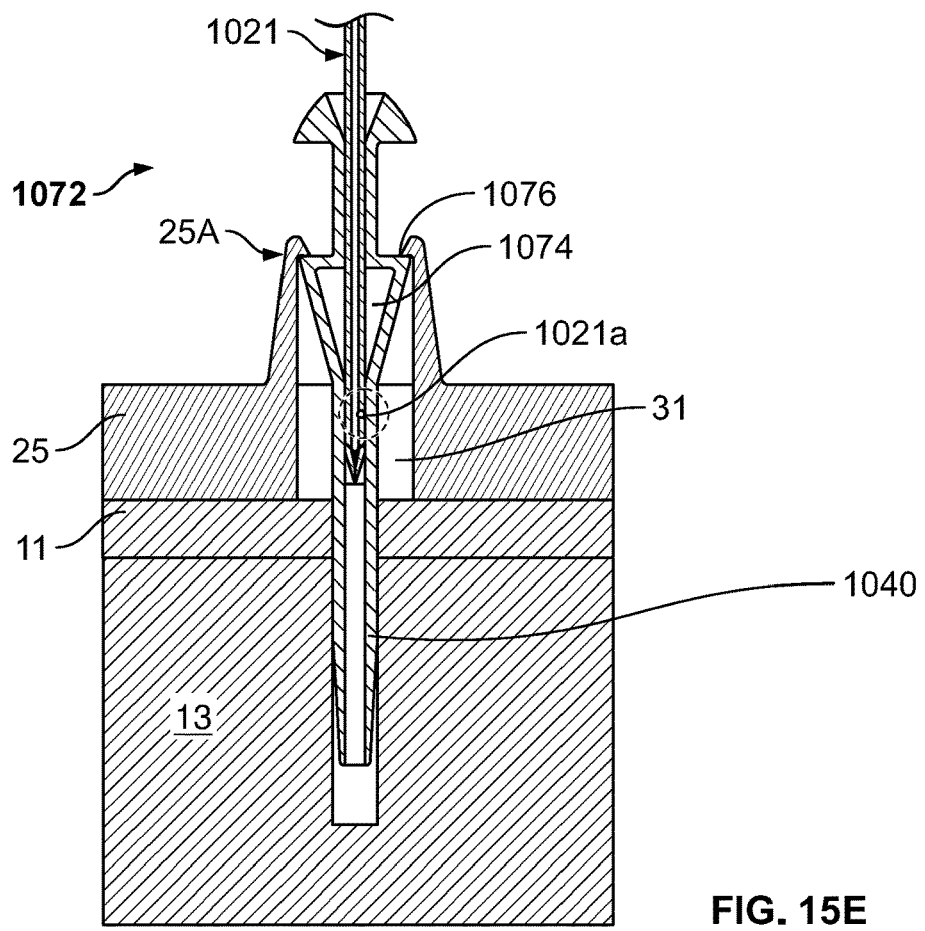
Figure 15F:
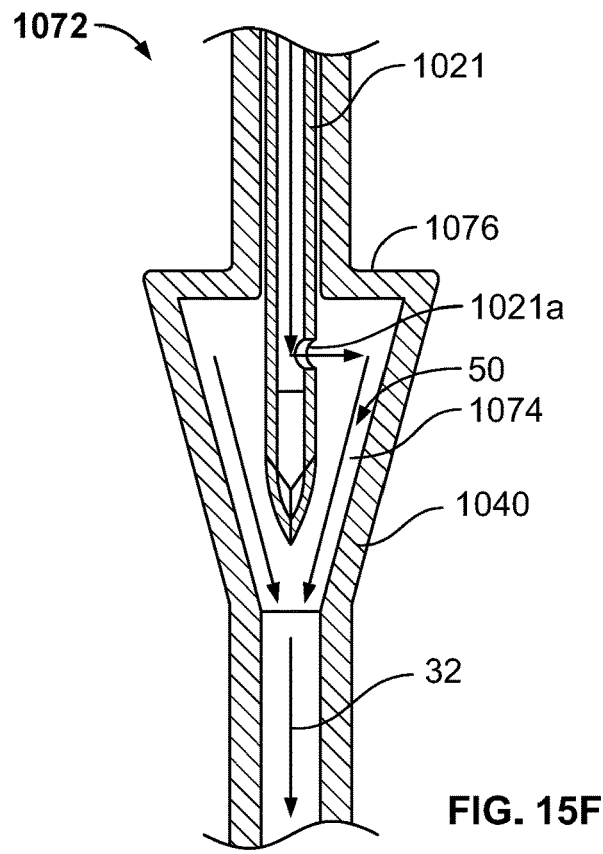

As illustrated in FIG. 15E, the needle 1021 is then moved to the "valve closed" position where the fluid port 1021a is sealed against the inside surface of the cannula 1040. When delivery of the drug 32 is desired, as illustrated in FIG. 15F, the needle 1021 is moved to a position where the fluid port 1021a is positioned within the valve chamber 1074. As a result, the fluid path 50 is again hydraulically connected to the cannula 1040, thus allowing the drug 32 to be administered.

Figure 15G:
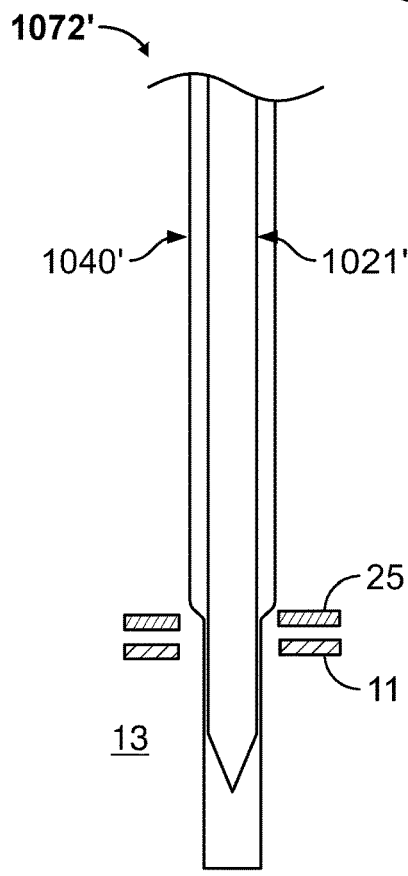
Figure 15H:
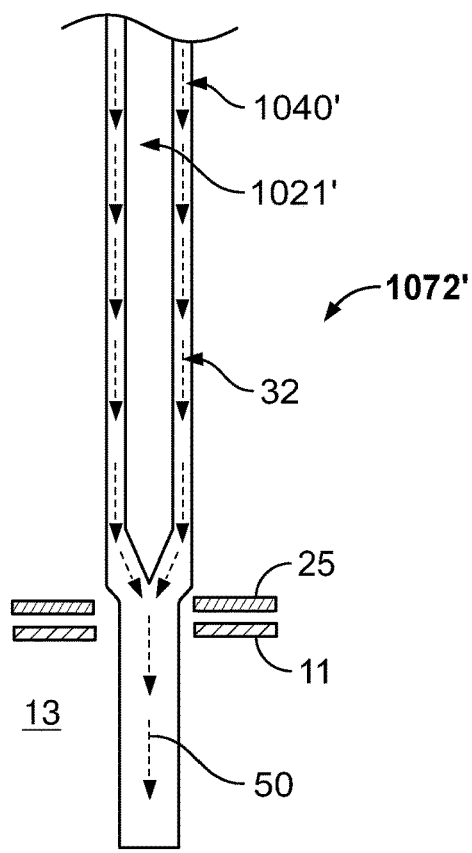

As illustrated in FIGS. 15G and 15H, an alternative flow restrictor 1072' is provided that uses a solid trocar 1021' in place of the needle 1021 provided in FIGS. 15A-15F. In these examples, drug flow is selectively enabled or blocked by the fit between the trocar 1021' and the cannula 1040'. In these examples, the trocar 1021' lacks a fluid pathway; and rather, the drug 32 flows around the outside surface of the trocar 1021' to be delivered to the patient. As a result, the trocar 1021' acts as an operable plug or seal with the cannula 1040'.

FIGS. 16A-16D illustrate an eleventh example of a flow restrictor 1172 corresponding to the flow restrictor 72 illustrated in FIGS. 4A and 4B, and more particularly, to the flow restrictor 772 illustrated in FIGS. 11A-12. Generally speaking, air contained within the drug reservoir 30 can result in blood and interstitial fluid entering the fluid path 50 after insertion of the needle. When a blood capillary ruptures during needle insertion and forms a clot that can occlude the fluid path 50, successful dose delivery may be adversely impacted. It can be time-consuming to request healthcare professionals to purge the air from the prefilled syringe used to add the drug 32 to the reservoir, and can result in squirting drug 32 out of the syringe, which creates waste.

In the illustrated example, the flow restrictor 1172 is in the form of a multi-chambered air filter mechanism having a main chamber 1174 and a secondary chamber 1176, an inlet 1173, and an outlet 1182. Further, positioned adjacent to the first chamber 1174 is a first membrane 1178 that is constructed from a hydrophilic material. The flow restrictor 1172 further accommodates a second membrane 1180 constructed from a hydrophobic material. Hydrophobic membranes have a critical water break-through pressure, below which water (and therefore, drug 32) cannot pass through. Similarly, hydrophilic membranes also have a critical pressure, below which air cannot pass through. This critical pressure is known as a bubble point pressure. The flow restrictor 1172 is designed to ensure the drug 32 will not escape the air filter outlet, and that air bubbles cannot be extruded with the drug 32 during delivery. Additionally, the hold volume, or the drug retained within the device, may be minimized (e.g., less than approximately 20 µL in some examples) due to the exclusion of air bubbles.

Figure 16A:
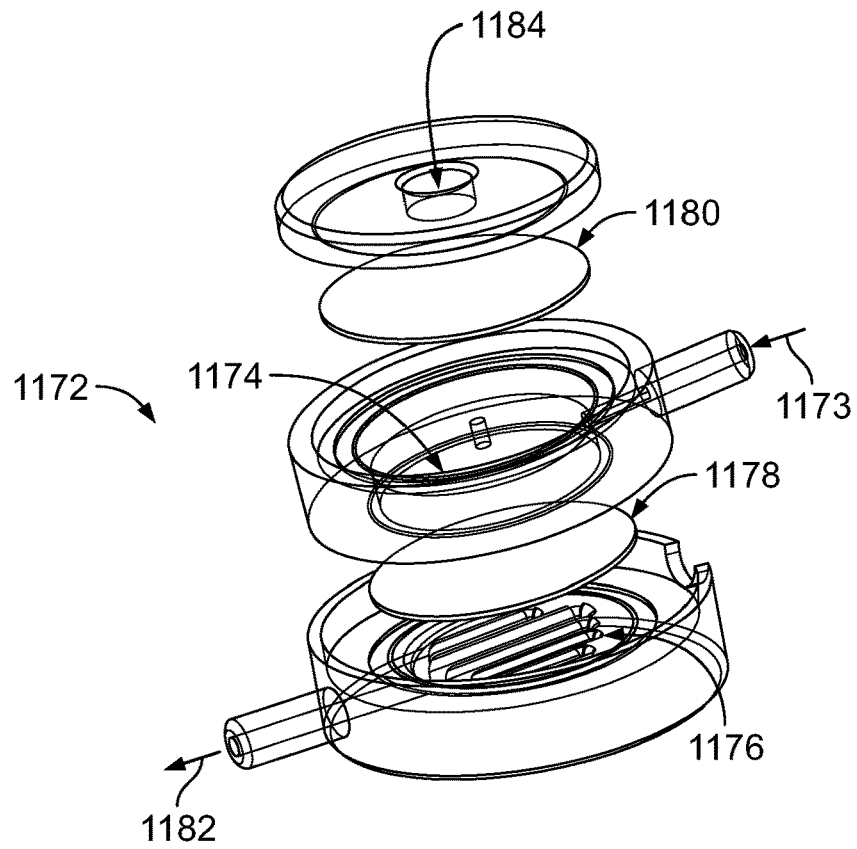
FIGS. 16A-16D illustrate an eleventh backflow prevention mechanism using an alternative air exclusion device in accordance with various embodiments.
Figure 16B:
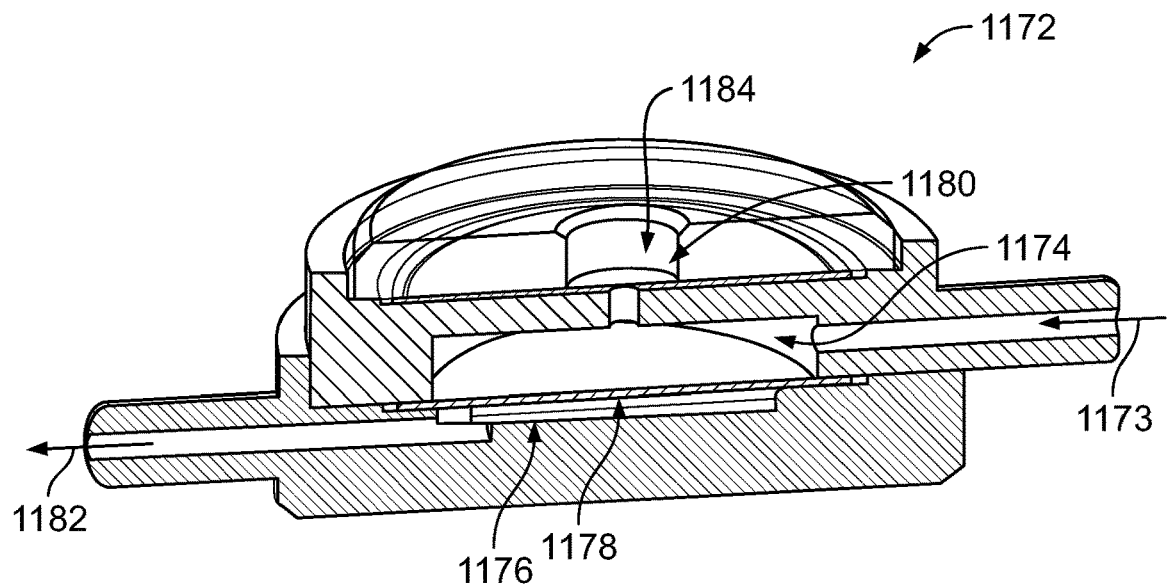

As illustrated in FIGS. 16A and 16B, during filling of the device 10, a drug 32 and air enter the main chamber 1174 via inlet 1173. The drug 32 passes through the first, hydrophilic membrane 1178 to the secondary chamber 1176 and is then sent to an outlet 1182 for delivery (e.g., extruded through the needle (not shown)). The air is filtered through the secondary, hydrophobic membrane 1180 and out to the atmosphere via an atmospheric outlet 1184.

By using the described air exclusion device 1172, air is removed from the fluid path 50, thus resulting in a fully primed fluidic path 50 with no air bubbles within the drug reservoir. Such fully primed fluid paths 50 reduce failures due to blood clot occlusions, thus increasing the reliability of the device and ensuring successful delivery of a full dose of drug 32.

Figure 16C:
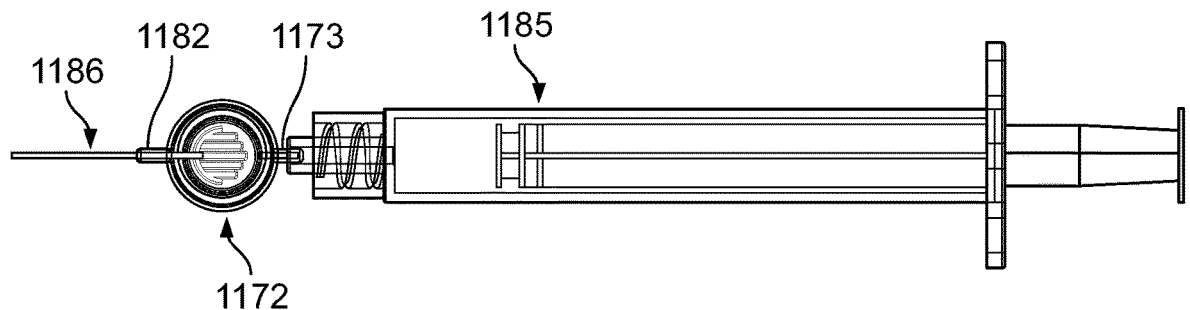
Figure 16D:
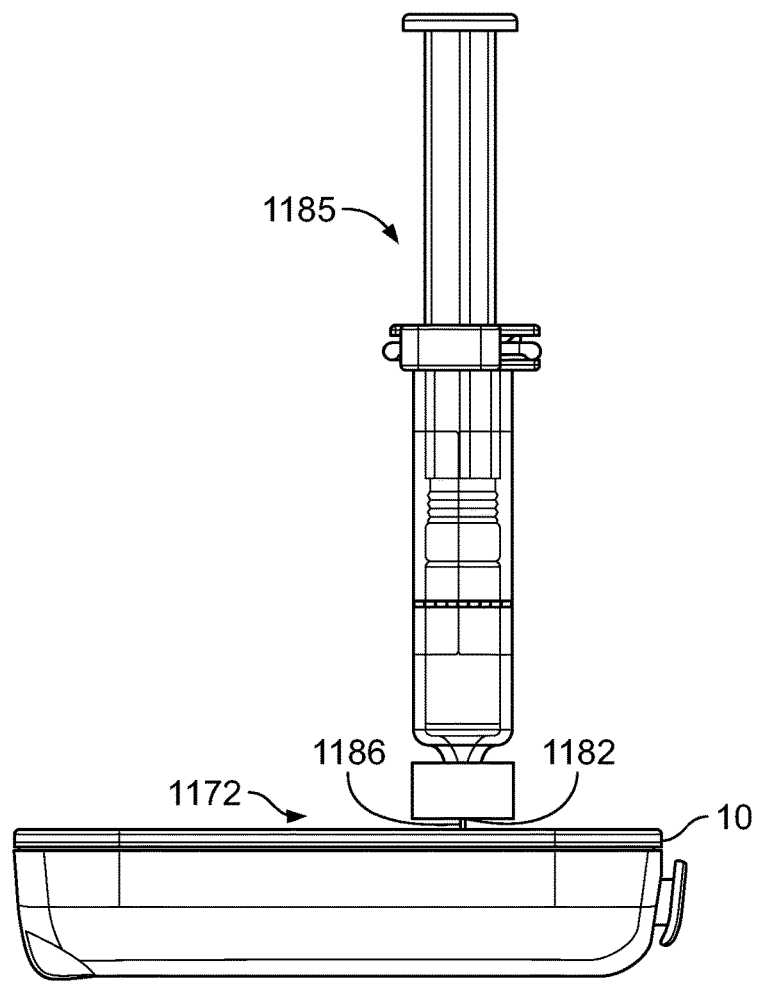

In some forms, the air exclusion device 1172 can be integrated directly into the device (e.g., coupled to an inlet port of the reservoir 30 within the housing), or alternatively, in some examples, the air exclusion device 1172 can be selectively coupled to the exterior of the device 10 at a drug delivery port that is in fluid communication with the reservoir 30. For example, as illustrated in FIGS. 16C and 16D, the air exclusion device 1172 may be added to the tip of a filling syringe 1185. The outlet 1182 of the air exclusion device 1172 may have a needle 1186 that is inserted into the device 10 to fill the drug 32 into the reservoir 30. The air exclusion device 1172 may include a Luer lock mechanism used to secure to the filling syringe 1185. Other examples are possible.

In some examples, additional strategies may be used to reduce and/or eliminate clot formation. For example, a desired pressure may be applied via the device 10 that is capable of clearing any potential clots. In some approaches, by using a primed fluid path, any potential clots may be cleared after a desired delay (e.g., between approximately 25 and approximately 30 hours) by applying a pressure of approximately 10 psi. It is noted that the location of the clot may have an impact on the required pressure needed to clear the clot. For example, if the clot is only disposed within the cannula (as opposed to being disposed within the cannula and the needle), the likelihood of clearing the clot using approximately 10 psi of pressure is greater. However, if the clot extends upstream of the needle or forms within the flexible tubing 52, it is less likely that it may be cleared via the application of pressure.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamoylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker); Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
    a housing defining a shell and an inner volume;
    a container at least partially disposed within the housing, the container having an inner volume adapted to contain a medicament to be administered to a user;
    a drive mechanism at least partially disposed within the housing, the drive mechanism adapted to exert a force to urge the medicament out the container;
    a needle assembly at least partially disposed within the housing, the needle assembly adapted to insert a needle or a trocar into the user's skin and to subsequently retract, thereby leaving a cannula within the user's skin for a period of time at least until the drive mechanism urges the medicament out the container;
    a fluid flow connection coupled to the container and the needle assembly, the fluid flow connection adapted to allow the medicament to flow from the container to the needle assembly; and
    a backflow prevention mechanism disposed within a coupling region between the container and the needle assembly, the backflow prevention mechanism comprising at least one flow restrictor to restrict a fluid from flowing from the cannula to the container, thereby reducing and/or eliminating clot formation during the period of time at least until the drive mechanism urges the medicament from the container to the needle assembly,
    wherein the coupling region includes an upstream portion and a downstream portion, the upstream portion having an upstream diameter larger than the flow restrictor and the downstream portion having a downstream diameter smaller than the flow restrictor.

2. The drug delivery device of claim 1, wherein the at least one flow restrictor comprises a one-way valve.

3. The drug delivery device of claim 2, wherein the at least one flow restrictor comprises at least one of:
    a slit valve;
    an umbrella valve;
    a ball valve;
    a duckbill valve; or
    a flap valve.

4. The drug delivery device of claim 1, wherein the at least one flow restrictor comprises an air exclusion device.

5. The drug delivery device of claim 1, wherein the backflow prevention mechanism is disposed at a coupling region at which the fluid flow connection is coupled to the needle assembly.

6. The drug delivery device of claim 5, wherein the coupling region comprises a ball and reservoir receptacle adapted to seal the needle assembly.

7. The drug delivery device of claim 1, wherein the fluid flow connection is constructed from a flexible tube.

8. The drug delivery device of claim 7, wherein the flexible tube is constructed from a polymer material.

9. A backflow prevention mechanism for a drug delivery device, the backflow prevention mechanism disposed within a coupling region between a container and the needle assembly, the backflow prevention mechanism comprising at least one flow restrictor to selectively restrict a fluid from flowing from a cannula to the container over an extended period of time after a needle assembly delivers the cannula within a user's skin, thereby reducing and/or eliminating clot formation,
    wherein the coupling region includes an upstream portion and a downstream portion, the upstream portion having an upstream diameter larger than the flow restrictor and the downstream portion having a downstream diameter smaller than the flow restrictor.

10. The backflow prevention mechanism of claim 9, wherein the at least one flow restrictor comprises a one-way valve.

11. The backflow prevention mechanism of claim 9, wherein the one-way valve comprises at least one of:
    a slit valve;
    an umbrella valve;
    a ball valve;
    a duckbill valve; or
    a flap valve.

12. The backflow prevention mechanism of claim 9, wherein the at least one flow restrictor comprises an air exclusion device.

13. A method of preventing backflow in a drug delivery device having a backflow prevention mechanism, the drug delivery device including housing defining a shell and an inner volume and a container at least partially disposed within the inner volume of the housing and being adapted to contain a medicament to be administered to a user, the method comprising:
- at least partially disposing a drive mechanism within the housing, the drive mechanism adapted to exert a force to urge the medicament out of the container;
- at least partially disposing a needle assembly within the housing, the needle assembly adapted to insert a needle or a trocar into the user's skin and to subsequently retract, thereby leaving a cannula within the user's skin for a period of time at least until the drive mechanism urges the medicament out the container;
- coupling a fluid flow connection to the container and the needle assembly to allow the medicament to flow from the container to the needle assembly; and
- disposing a backflow prevention mechanism within a coupling region between the container and the needle assembly, the backflow prevention mechanism comprising at least one flow restrictor that restricts a fluid from flowing from the cannula to the container, thereby reducing and/or eliminating clot formation during the period of time at least until the drive mechanism urges the medicament from the container to the needle assembly.

14. The method of claim 13, wherein associating the at least one backflow prevention mechanism comprises associating a one way valve with the at least one of the container, the fluid flow connection, or the needle assembly.

15. The method of claim 13, wherein associating the at least one backflow prevention mechanism comprises associating an air exclusion device with the at least one of the container, the fluid flow connection, or the needle assembly.

16. The method of claim 13, wherein the backflow prevention mechanism is disposed at a coupling region at which the fluid flow connection is coupled to the needle assembly.

* * * * *